United States Patent [19]
Goldstein

[11] Patent Number: 5,891,994
[45] Date of Patent: Apr. 6, 1999

[54] METHODS AND COMPOSITIONS FOR IMPAIRING MULTIPLICATION OF HIV-1

[75] Inventor: Gideon Goldstein, Short Hills, N.J.

[73] Assignee: Thymon L.L.C., Short Hills, N.J.

[21] Appl. No.: 893,853

[22] Filed: Jul. 11, 1997

[51] Int. Cl.$^6$ .......................... A61K 38/04; A61K 38/00; C07K 1/00; C07K 17/00
[52] U.S. Cl. .......................... 530/329; 530/350; 530/324; 530/325; 530/326; 530/327; 530/328; 424/184.1; 424/188.1; 424/204.1; 424/208.1
[58] Field of Search .............................. 424/188.1, 184.1, 424/204.1, 208.1; 530/350, 324, 325, 326, 327, 328, 329

[56] References Cited

U.S. PATENT DOCUMENTS

| | | | |
|---|---|---|---|
| 4,871,488 | 10/1989 | Mannino et al. | 264/4.6 |
| 5,019,510 | 5/1991 | Wain-Hobson . | |
| 5,110,802 | 5/1992 | Cantin et al. | 514/44 |
| 5,158,877 | 10/1992 | Edwards et al. | 435/91 |
| 5,238,822 | 8/1993 | Dykes et al. | 435/69.1 |
| 5,597,895 | 1/1997 | Gaynor . | |
| 5,606,026 | 2/1997 | Rodman . | |
| 5,674,980 | 10/1997 | Frankel . | |

FOREIGN PATENT DOCUMENTS

| | | |
|---|---|---|
| WO87/02989 | 5/1987 | WIPO . |
| WO91/09958 | 7/1991 | WIPO . |
| WO91/10453 | 7/1991 | WIPO . |
| WO92/07871 | 5/1992 | WIPO . |
| WO92/14755 | 9/1992 | WIPO . |
| WO95/31999 | 11/1995 | WIPO . |

OTHER PUBLICATIONS

Brake, et al, "Characterization of murine monoclonal antibodies . . . " J. Virol. 64(2): 962–965, 1990.

Primary Examiner—Lynette F. Smith
Assistant Examiner—Brett Nelson
Attorney, Agent, or Firm—Howson and Howson

[57] ABSTRACT

A composition is provided which contains a non-naturally occurring peptide or polypeptide comprising at least two or more, and preferably all four amino acid sequences -Asp-Pro-Arg-Leu-Glu-Pro- SEQ ID NO: 6; -Asp-Pro-Lys-Leu-Glu-Pro- SEQ ID NO: 7; -Asp-Pro-Ser-Leu-Glu-Pro- SEQ ID NO: 8; and -Asp-Pro-Asn-Leu-Glu-Pro- SEQ ID NO: 9. This composition, including a number of additional optional peptides or polypeptides, and in a variety of forms, demonstrates a biological activity of inducing antibodies that react with most HIV-1 Tat proteins and impairing the multiplication of HIV-1. Also provided are synthetic genes encoding these peptides, recombinant viruses and commensal bacterium carrying these genes, transfected host cells, and polyclonal or other types of antibodies produced by immunizing other mammals with these aforementioned compositions. Methods for making and using such compositions to lower the viral level of HIV-1 are described.

35 Claims, 4 Drawing Sheets

```
            Sst I                     Bam HI
              |                         |
GAG CTC TAC AAA TCC GGG GAT CCG GGT GAA GAT CCG CGT TTA
Glu Leu Tyr Lys Ser Gly Asp Pro Gly Glu Asp Pro Arg Leu
 1           5                      10

Xma I
                      | Sma I
                      |   |
GAG CCG TGG AAA CAC CCG GGT TCT GGT TCT GTT GAC CCT AAC
Glu Pro Trp Lys His Pro Gly Ser Gly Ser Val Asp Pro Asn
 15            20                      25

BspM II
                                   |
CTT GAA CCT TGG AAG CAT CCT GGC AGC TCC GGA GTC GAT CCC
Leu Glu Pro Trp Lys His Pro Gly Ser Ser Gly Val Asp Pro
     30              35                      40

Xho I
       |
AAA CTC GAG CCC TGG AAA CAC CCC GGA AGT TCG GGG GTA GAC
Lys Leu Glu Pro Trp Lys His Pro Gly Ser Ser Gly Val Asp
         45              50                      55
            Nco I                     PfiM I
              |                         |
CCA TCT CTG GAA CCA TGG AAG CAT CCA GGG AGT GGT AGC GTG
Pro Ser Leu Glu Pro Trp Lys His Pro Gly Ser Gly Ser Val
             60                      65                      70

Xma I
                               | Sma I
                               |   |
AAT CCG TCA TTA GAG CCG TGG AAA CAC CCG GGT TCA TCT GGA
Asn Pro Ser Leu Glu Pro Trp Lys His Pro Gly Ser Ser Gly
             75                      80

GTT GAT CCT CGC TTG GAA CCT TGG GAG CAT CCT GGT TCG TCC
Val Asp Pro Arg Leu Glu Pro Trp Glu His Pro Gly Ser Ser
 85              90                      95

GGT GTA GAC CCC CGA CTT GAG CCC TGG AAT CAC CTC GGG AGT
Gly Val Asp Pro Arg Leu Glu Pro Trp Asn His Leu Gly Ser
         100             105                     110
```

FIGURE 2B

```
TCA GGC GTA GAT CAT CGG CTC GAA CCA TGG AAA CAT CCA GGT
Ser Gly Val Asp His Arg Leu Glu Pro Trp Lys His Pro Gly
        115             120             125
```

```
                              Alwn I
                              PfiM I  Bgl II       OxaN I
Nco I                            |      |            |
 |                               |      |            |
TCT GGA GAT CTG CGC CAG CGG CGA CGT ACT CCT CAG GAT TCT
Ser Gly Asp Leu Arg Gln Arg Arg Arg Thr Pro Gln Asp Ser
            130             135             140
```

```
                      Nar I
          Tth I         |  Bbe I                OxaN I
            |           |    |                    |
GGA TCT CGA CAA CGT CGG CGC CCT CCC CAA GAC TCC TCA GGA
Gly Ser Arg Gln Arg Arg Arg Pro Pro Gln Asp Ser Ser Gly
                145             150
```

```
CGG CAG CGC CGA CGA CCC CCA CAG GGT TCA GGT TCA CGT CAA
Arg Gln Arg Arg Arg Pro Pro Gln Gly Ser Gly Ser Arg Gln
155             160             165
```

```
        Tth I
          |
CGA CGC GGT CCA CCC CAA GGC TCG GGT TCG CGC CAG CGG CGA
Arg Arg Gly Pro Pro Gln Gly Ser Gly Ser Arg Gln Arg Arg
        170             175             180
```

```
        Aat II                          Tth I
          |                               |
CGT CCG CCT CAG AAC TCT AGT GGA CGA CAA CGT CGG CGC TCT
Arg Pro Pro Gln Asn Ser Ser Gly Arg Gln Arg Arg Arg Ser
        185             190             195
```

```
CCC CAA GAT TCC GGC GGG CGG CAG CGC CGT CGA TCA CCA CAG
Pro Gln Asp Ser Gly Gly Arg Gln Arg Arg Arg Ser Pro Gln
            200             205             210
```

```
AAC TCA GGT GGG CGT CAA CGA CGC CGG ACT CCG CAA TCT TCA
Asn Ser Gly Gly Arg Gln Arg Arg Arg Thr Pro Gln Ser Ser
            215             220
```

FIGURE 2C

```
       Xma III
        |
TCC  GGC  CGC  CAG  CGG  CGA  CGT  GCC  CAT  CAG  AAT  AGC  GGC  AGC
Ser  Gly  Arg  Gln  Arg  Arg  Arg  Ala  His  Gln  Asn  Ser  Gly  Ser
225                      230                 235

Tth            BssH II
        |              |
CGA  CAA  CGT  CGG  CGC  GCA  CAC  CAA  GAC  AGC  AGT  GGG  CGG  CAG
Arg  Gln  Arg  Arg  Arg  Ala  His  Gln  Asp  Ser  Ser  Gly  Arg  Gln
          240                 245                 250

CGC  CGT  CGA  GCG  CCT  GAA  GAT  AGT  GGT  TCT  CGT  CAA  CGA  CGC
Arg  Arg  Arg  Ala  Pro  Glu  Asp  Ser  Gly  Ser  Arg  Gln  Arg  Arg
               255                 260                 265

BspMII                           ApaLI
                          |                                |
CGG  GCT  CCC  CCT  GAC  AGC  TCC  GGA  CGC  CAG  CGG  CAA  CGT  GCA
Arg  Ala  Pro  Pro  Asp  Ser  Ser  Gly  Arg  Gln  Arg  Gln  Arg  Ala
               270                 275                      280

OxaNI
                |
CCA  GAT  AGT  TCC  TCA  GGT  CAT  CAC  CAC  CAT  CAT  CAC   TAATAA
Pro  Asp  Ser  Ser  Ser  Gly  His  His  His  His  His  His
                    285                      290

EcoR I  Bam HI  Xba I           Sal I   Hind III
 |       |       |               |       |
GAA  TTC  GGA  TCC  TCT  AGA  GTC  GAC  AAG  CTT   912
Glu  Phe  Gly  Ser  Ser  Arg  Val  Asp  Lys  Leu
          295
```

METHODS AND COMPOSITIONS FOR IMPAIRING MULTIPLICATION OF HIV-1

FIELD OF THE INVENTION

The present invention relates generally to compositions and methods useful for inhibiting the multiplication of human immunodeficiency virus-1 (HIV-1) in infected patients, symptomatic or asymptomatic, and for attenuating HIV-1 multiplication during primary infection in previously uninfected subjects, thus minimizing progression to AIDS.

BACKGROUND OF THE INVENTION

High plasma levels of human immunodeficiency virus type 1 (HIV-1) RNA are found during primary infection with HIV-1, the seroconversion illness, [C. Baumberger et al, *AIDS*, 7:(suppl 2):S59 (1993); M. S. Saag et al, *Nature Med.*, 2:625 (1996)], after which they subside as the immune response controls the infection to a variable extent. Post seroconversion, lower but detectable levels of plasma HIV-1 RNA are present, and these levels rise with disease progression to again attain high levels at the AIDS stage [M. S. Saag et al, *Nature Med.*, 2:265 (1996)]. Approximately 50% of subjects have a symptomatic illness at seroconversion [B. Tindall and D. A. Cooper, *AIDS*, 5:1 (1991)] and symptomatic seroconversion is associated with an increased risk for the development of AIDS, probably because a severe primary illness is likely related to an early and extensive spread of HIV.

Inhibition of viral multiplication during the initial infection will likely reduce the subsequent development of chronic viremia leading to AIDS. Current medical practice, with administration of antiviral drugs for defined "at risk" situations, such as needle sticks with contaminated blood or pregnancy in HIV infected mothers, supports this concept.

Post sero-conversion levels of HIV-1 RNA in plasma have proven to be the most powerful prognosticator of the likelihood of progression to AIDS [J. W. Mellors et al, *Science*, 272:1167 (1996); M. S. Saag et al, *Nature Med.*, 2:265 (1996); R. W. Coombs et al, *J. Inf. Dis.*, 174:704 (1996); S. L. Welles et al, *J. Inf. Dis.*, 174:696 (1990)]. Other measures of viral load, such as cellular RNA [K. Saksela et al, *Proc. Natl. Acad. Sci. USA*, 91:1104 (1994)] and cellular HIV proviral DNA [T-H. Lee et al, *J. Acq. Imm. Def. Syndromes*, 7:381 (1994)] similarly establish the importance of the initial infection in establishing viral loads that determine future disease progression.

Thus, any intervention that inhibits HIV-1 infectivity during initial infection and/or lowers viral load post seroconversion is likely to have a favorable influence on the eventual outcome, delaying or preventing progression to AIDS.

A variety of methods are now employed to treat patients infected with human immunodeficiency virus (HIV-1), including treatment with certain combinations of protease inhibitor drugs. Unfortunately, however, this type of treatment is associated with serious side effects in some patients.

Alternatively, vaccines are under development for control of the spread of HIV-1 to uninfected humans. However, this effort has largely been directed to proteins of the virus, expressed on the surface of infected cells, which are recognized by cytotoxic T cells with elimination of the infected cells, while free virus is blocked and cleared by antibody to surface antigens of the virion. Limitations of this mode of vaccination are readily apparent for HIV-1, which has demonstrated a great diversity in immunogenic viral epitopes and rapid mutational variations that occur within and between individuals [B. D. Preston et al., *Science*, 242:1168 (1988); J. D. Roberts et al., *Science*, 242:1171 (1988); A. R. Meyerhans et al., *Cell*, 58:901 (1989); K. Kusumi et al., *J. Virol.*, 66:875 (1992); B. A. Larder et al., *Science*, 243:1731 (1989); M. S. Sang et al., *N. Engl. J. Med.*, 329:1065 (1993); M. A. Sande, et al., *JAMA*, 270:2583 (1993); M. Seligmann et al., *Lancet*, 343:871 (1994); G. Meyers et al., Human retroviruses and AIDS 1993, I-V. A compilation and analysis of nucleic acid and amino acid sequences. Los Alamos National Laboratory, Los Alamos, N.Mex.]

Variation in strains of HIV-1 and frequent mutations of virion proteins have prevented successful application of conventional vaccine approaches [W. E. Paul, *Cell*, 82:177 (1995); J. E. Osborn, *J. Acq. Imm. Def. Syndr. Hum. Retrovirol.*, 9:26 (1995)]. Mutation and selection of resistant variants is the central problem in developing a successful HIV-1 vaccine [M. D. Daniel et al., *Science*, 258:1938 (1992); N. L. Letvin, *N. Engl. J. Med.*, 329:1400 (1993); M. Clerici et al., *AIDS*, 8:1391 (1994); S. M. Wolinsky et al, *Science*, 272:537 (1996)].

Other approaches to HIV-1 treatment have focused on the transactivating (tat) gene of HIV-1, which produces a protein (Tat) essential for transcription of the virus. The tat gene and its protein have been sequenced and examined for involvement in proposed treatments of HIV [see, e.g., U.S. Pat. No. 5,158,877; U.S. Pat. No. 5,238,882; U.S. Pat. No. 5,110,802; International Patent Application No. WO92/07871, published May 14, 1992; International Patent Application No. WO91/10453, published Jul. 25, 1991; International Patent Application No. WO91/09958, published Jul. 11, 1991; International Patent Application No. WO87/02989, published May 21, 1987]. Tat protein is released extracellularly, making it available to be taken up by other infected cells to enhance transcription of HIV-1 in the cells and to be taken up by noninfected cells, altering host cell gene activations and rendering the cells susceptible to infection by the virus. Uptake of Tat by cells is very strong, and has been reported as mediated by a short basic sequence of the protein [S. Fawell et al., *Proc. Natl. Acad. Sci., USA*, 91:664–668 (1994)].

International Patent Application No. WO92/14755, published Sep. 3, 1992, relates to the Tat protein and to the integrin cell surface receptor capable of binding to the Tat protein. Two Tat sequences that bind integrin are identified, which are the basic region or domain which is the dominant binding site for the integrin, having a peptide sequence of -Arg-Lys-Lys-Arg-Arg-Gln-Arg-Arg-Arg- [SEQ ID NO: 4], as well as -Gly-Arg-Gly-Asp-Ser-Pro- [SEQ ID NO: 5]. This specification demonstrates that a number of peptides corresponding to these Tat sequences and the corresponding integrins block in vitro cell binding to Tat coated plates, as do antibodies to the appropriate integrins. However, the specification also shows that these reagents do not block uptake of functional Tat by cells (see Example 9 in WO92/14755), thus nullifying the proposed mechanism of action for therapeutic benefit in HIV infection. The Tat sequences described in this international application are distinct from the peptide immunogens of the present invention.

Both monoclonal and polyclonal antibodies to Tat protein have been readily produced in animals and shown to block uptake of Tat protein in vitro [see, e.g., D. Brake et al, *J. Virol.*, 64:962 (1990); D. Mann et al, *EMBO J.*, 10:1733 (1991); J. Abraham et al, cited above; P. Auron et al, cited above; M. Jaye et al, cited above; G. Zauli et al, cited above]. More recent reports showed that monoclonal or polyclonal antibodies to Tat protein added to tissue culture medium attenuated HIV-1 infection in vitro [L. Steinaa et al, *Arch. Virol.*, 139:263 (1994); M. Re et al, *J. Acq. Imm. Def. Syndr. Hum. Retrovirol.*, 10:408 (1995); and G. Zauli et al, *J. Acq. Imm. Def. Syndr. Hum. Retrovirol.*, 10:306 (1995)].

The inventor's own publication [G. Goldstein, *Nature Med.*, 2:960 (1996); see also, International Patent Application No. WO95/31999, published Nov. 30, 1995] reviewed the evidence indicating that secretion of HIV-1 Tat protein from infected cells and uptake by both infected and uninfected cells was important for the infectivity of HIV-1. Previous studies also showed that antibodies to Tat protein in vitro blocked uptake of Tat and inhibited in vitro infectivity. Goldstein proposed active immunization of mammals to induce antibodies to HIV-1 Tat protein as a potential AIDS vaccine.

Despite the growing knowledge about HIV-1 disease progression, there remains a need in the art for the development of compositions and methods for treatment of HIV-1, both prophylactically and therapeutically, which are useful to lower the viral levels of HIV-1 for the treatment and possible prevention of the subsequent, generally fatal, AIDS disease.

SUMMARY OF THE INVENTION

In one aspect, the invention provides novel compositions designed to induce antibodies reactive with almost all known variants of HIV-1 Tat protein. In one embodiment the composition contains a non-naturally occurring peptide or polypeptide, which contains or has embedded in the peptide/polypeptide sequence, at least two, and preferably all four, amino acid sequences selected from -Asp-Pro-Arg-Leu-Glu-Pro-; -Asp-Pro-Lys-Leu-Glu-Pro; -Asp-Pro-Ser-Leu-Glu-Pro-; and -Asp-Pro-Asn-Leu-Glu-Pro- [SEQ ID NOS: 6 through 9, respectively]. This composition demonstrates a biological activity of inducing in immunized mammals antibodies that react with most variants of Tat proteins and impair the multiplication of HIV-1 in an acute infection, thus preventing high post-seroconversion plasma levels of HIV-1 that are associated with progression to AIDS. The peptides or polypeptides of these compositions are produced synthetically or recombinantly.

In another aspect, the above-described composition further contains one or more additional peptide or polypeptide (s) which represent other amino acid sequences which correspond to amino acid residues 5 to 10 of an HIV-1 Tat protein. These optional amino acid sequences are described in detail below. These sequences are preferably from an HIV-1 strain with a Tat protein variant at that location.

In still another aspect, the above-described composition further contains one or more additional peptide or polypeptide(s) which represent amino acid sequences which correspond to amino acid residues 56 to 62 of an HIV-1 Tat protein. Such other optional immunogenic peptides and polypeptides may contain at least one copy of an amino acid sequence of the formula -Arg-Arg-X-Pro-Gln-Y-Ser- [SEQ ID NO: 10], as described in detail below. Other peptides or polypeptides representative of aa 56–62, but having different sequences from that of the above formula may also be included in the composition.

In one embodiment, the composition described above comprises a peptide or polypeptide which contains multiple repeats of one of the above-described amino acid sequences. In another embodiment, the composition comprises a peptide or polypeptide containing sequentially multiple different amino acid sequences. Still another embodiment of the composition comprises peptides or polypeptides which contain different amino acid sequences repeated multiple times.

In another aspect, the invention provides a composition as above-described wherein each peptide or polypeptide is coupled to the same or different carrier protein.

In still a further aspect, the composition provides the peptides or polypeptides in the form of a multiple antigenic peptide.

In yet a further aspect, the invention provides a synthetic gene which encodes sequentially a peptide or polypeptide that contains at least two and preferably all four, amino acid sequences selected from -Asp-Pro-Arg-Leu-Glu-Pro-; -Asp-Pro-Lys-Leu-Glu-Pro; -Asp-Pro-Ser-Leu-Glu-Pro-; and -Asp-Pro-Asn-Leu-Glu-Pro- [SEQ ID NOS: 6 through 9, respectively], or multiple copies of any of these sequences. Synthetic genes which encode any of the peptides or polypeptides above-described are also provided. The synthetic gene may contain each amino acid sequence separated by a spacer sequence, or may express each peptide/polypeptide in an open reading frame with a carrier protein. Alternatively the synthetic gene may be separated from the carrier protein by a spacer.

In yet a further aspect, the invention provides a synthetic molecule comprising the above-described synthetic gene, operatively linked to regulatory nucleic acid sequences, which direct and control expression of the product of the synthetic gene in a host cell.

In another aspect, the invention provides a recombinant virus which contains the above described synthetic gene or synthetic molecule, which virus is capable of expressing multiple copies of the product of the gene or molecule in a host cell. The virus is non-pathogenic to humans.

In yet another aspect, the invention provides a commensal bacterium which contains the above described synthetic gene or synthetic molecule, which bacterium is capable of expressing multiple copies of the product of the gene or molecule and inducing antibodies in a mammalian host.

In still a further aspect, the invention provides an isolated antibody composition which is directed against a non-naturally occurring peptide or polypeptide comprising at least two or more copies of an amino acid sequence, selected from the group consisting of [SEQ ID NOS: 6 through 9, respectively]:

-Asp-Pro-Arg-Leu-Glu-Pro-;
-Asp-Pro-Lys-Leu-Glu-Pro-;
-Asp-Pro-Ser-Leu-Glu-Pro-; and
-Asp-Pro-Asn-Leu-Glu-Pro-.

The antibody may be directed against the other optional immunogens contained in a peptide or polypeptide of this invention, including those of formula -Arg-Arg-X-Pro-Gln-Y-Ser- [SEQ ID NO: 10]. This antibody is produced by immunizing a mammal with a peptide/polypeptide composition of the invention, a synthetic gene or synthetic molecule of the invention; a recombinant virus or commensal bacterium of the invention; and isolating and purifying antibody from said immunized mammal. Alternatively, the antibody may be a polyclonal antibody, a monoclonal antibody, a chimeric antibody, a humanized antibody, a human antibody, or mixtures thereof.

Thus, another aspect of the invention is a pharmaceutical composition useful for inducing antibodies that react with most HIV-1 Tat proteins and impair the multiplication of HIV-1. The pharmaceutical composition comprises at least one of the recombinant or synthetic peptide/polypeptide compositions described above; the synthetic gene/molecule described above; the recombinant virus described herein; or the commensal bacterium described herein, in a pharmaceutically acceptable carrier.

Still a further aspect of the invention is a pharmaceutical composition useful for impairing the multiplication of HIV-1, this composition containing an above described antibody composition.

In yet a further aspect of the invention, a method for reducing the viral levels of HIV-1 involves exposing a human to antibody-inducing pharmaceutical compositions described above, actively inducing antibodies that react with most HIV-1 Tat proteins, and impairing the multiplication of the virus in vivo. This method is appropriate for an HIV-1 infected subject with a competent immune system, or an uninfected or recently infected subject. The method induces antibodies which react with HIV-1 Tat proteins, which antibodies reduce viral multiplication during any initial acute infection with HIV-1 and minimize chronic viremia which leads to AIDS.

In still another aspect, the invention provides a method for reducing the viral levels of HIV-1 by administering to a human, who is incapable of mounting an effective or rapid immune response to infection with HIV-1, a pharmaceutical composition containing the antibody compositions described above. The method can involve chronically administering the composition.

Yet other aspects of the invention include methods for producing the compositions described above, as well as host cells transfected with such compositions.

Other aspects and advantages of the present invention are described further in the following detailed description of the preferred embodiments thereof.

BRIEF DESCRIPTION OF THE DRAWINGS

FIG. 1 illustrates an HIV-1 Tat protein consensus sequence [SEQ ID NO: 1], based on Tat protein sequences of 31 known HIV-1 strains found in the common B subtype [NIH Los Alamos database]. The amino acid positions in which variations appear are in lower case letters.

FIGS. 2A–2C illustrates a synthetic gene which encodes a fusion protein [SEQ ID NO: 3] of this invention, described in detail in Example 4 below.

DETAILED DESCRIPTION OF THE INVENTION

The present invention provides a solution to the above-stated problem by providing compositions which induce antibodies in uninfected or early stage infected subjects still capable of mounting an immune response to an immunogen, said antibodies reacting with most Tat proteins and inhibiting multiplication of HIV-1. This prevents further disease progression to AIDS. Antibody compositions are also provided for use in infected or non-infected humans, who are incapable of mounting an effective or rapid immune response to HIV-1 infection. These compositions are capable of reacting with most known Tat proteins, thus reducing viral levels of HIV-1, and thus are useful in both a therapeutic and prophylactic context to control the development of AIDS in a large population exposed to, or infected by, HIV-1 which produce upon infection different Tat proteins.

The compositions of the present invention may be proteinaceous in nature, or may be nucleic acid compositions which encode the peptides and polypeptides that induce antibodies to Tat, which in turn impair multiplication of HIV-1.

A. Peptide/Polypeptide Compositions

1. Primary Compositions

The present invention provides as its "primary composition", a composition containing a non-naturally occurring peptide or polypeptide, which comprises at least two "primary immunogens" or "primary amino acid sequences". By "immunogen" is meant any sequence or molecule which elicits a specific humoral immune response (for the purpose of this invention) in a mammal exposed to that molecule in vivo.

The primary immunogens of this invention are peptides or polypeptides which contain embedded in the peptide sequence, at least two of the following amino acid sequences [SEQ ID NOS: 6 through 9, respectively]:

-Asp-Pro-Arg-Leu-Glu-Pro-;
-Asp-Pro-Lys-Leu-Glu-Pro;
-Asp-Pro-Ser-Leu-Glu-Pro-; and
-Asp-Pro-Asn-Leu-Glu-Pro-.

Preferably, this primary composition contains a polypeptide which contains all four of these amino acid sequences. Such compositions may also contain multiple peptides or polypeptides which contain multiple copies of a single peptide, or multiple copies of different of these four peptides in any order, or multiple copies of one or two of these peptides. In any variation, it is preferred for the efficacy of the primary composition, that at least one copy of all four amino acid sequences are present. It is not important for the function of the composition, whether these amino acid sequences are present in one or more peptides or polypeptides.

The amino acid sequences identified above may be flanked by other amino acids in the primary immunogens; but the identity of the flanking amino acids is not essential to the biological function of the primary immunogen. These four amino acid sequences which are present in the primary immunogens correspond to amino acid residues 5–10 of the Tat consensus sequence [SEQ ID NO: 1] of FIG. 1 which is derived from a number of "Tat sequence variants". The term "Tat sequence variant" means a polypeptide or peptide containing Tat protein amino acid residues 5–10 (or a sequence from another HIV-1 strain Tat protein corresponding to that sequence of SEQ ID NO: 1) or Tat protein residues 56–62 (or a sequence from another HIV-1 strain Tat protein corresponding to that sequence of SEQ ID NO: 1). Each variant may differ from the consensus sequence of FIG. 1 [SEQ ID NO: 1] and/or from another variant by at least one amino acid change within those residues and provides an enhanced immune response to that particular Tat protein variant when added to the primary composition of the invention.

This primary composition demonstrates a biological activity of inducing antibodies to most Tat proteins, thereby impairing the multiplication of HIV-1 in a host cell or a host mammal. This primary composition elicits in an immune competent human, i.e., a non-infected human, or an asymptomatic infected human, an active immune response which is directed against most Tat protein variants of HIV-1. Active induction of antibodies in the early asymptomatic phase of HIV infection may reduce viral multiplication, lower the plasma viral load and reduce the likelihood of progression to AIDS. The composition which contains at least one primary immunogen with all four of the above amino acid sequences can elicit an immune response to about 97% of the 400 known Tat sequences of the common B subtypes of HIV-1 and with Tat proteins of all 18 non-B subtype HIV-1 that have been sequenced [courtesy of Dr. Esther Guzman, Los Alamos NIAID HIV database; GenBank database].

2. Additional Peptides and Polypeptides

The above-described primary composition of the invention may also be designed to contain a number of additional peptides or polypeptides, which contain other sequences which correspond to amino acid residues 5–10 of SEQ ID NO: 1 but are derived from other Tat variants which do not cross-react well with antibodies to the primary immunogens containing two to four of the above-described amino acid sequences. These additional peptides and polypeptides are referred to as "optional immunogens".

Optional immunogens which can be present in compositions of this invention, can contain at least one copy of at least one of the following amino acid sequences [SEQ ID NOS: 11 through 18, respectively]:
 -Gly-Pro-Arg-Leu-Glu-Pro-;
 -Ala-Pro-Arg-Leu-Glu-Pro-;
 -His-Pro-Arg-Leu-Glu-Pro-;
 -Asp-Pro-Gly-Leu-Glu-Pro-;
 -Asp-Pro-Arg-Ile-Glu-Pro-;
 -Asp-Pro-Arg-Leu-Gly-Pro-;
 -Asp-Pro-Arg-Leu-Glu-Ala-; and
 -Asn-Pro-Ser-Leu-Glu-Pro-.

Still other peptides/polypeptides which may be optionally present in a composition of this invention containing two, and preferably four of the sequences of the primary immunogens are still other optional immunogenic peptides and polypeptides, which may be derived from Tat variant protein sequences corresponding to amino acids 56–62 of SEQ ID NO: 1.

Among such optional immunogens are peptides and polypeptides that contain at least one copy of an amino acid sequence of the formula -Arg-Arg-X-Pro-Gln-Y-Ser- [SEQ ID NO: 10]. According to this formula, which is derived from Tat variant protein sequences corresponding to amino acids 56–62 of SEQ ID NO: 1, X may be Ala, Pro, Ser or Gln; and Y may be Asp, Asn, Gly or Ser. A preferred peptide/polypeptide in a composition of this invention contains the optional immunogen -Arg-Arg-Ala-Pro-Gln-Asp-Ser- [SEQ ID NO: 19]. Still other amino acid sequences which may be included in optional immunogens are -Arg-Arg-Ala-Pro-Pro-Asp-Ser-, -Arg-Arg-Ala-His-Gln-Asp-Ser- or -Arg-Arg-Ala-His-Gln-Asn-Ser- [SEQ ID NOS: 20 through 22, respectively].

Yet other amino acid sequences useful in optional immunogens for inclusion in the composition with the primary immunogens are -Arg-Arg-Pro-Pro-Gln-Asp-Asn, -Arg-Arg-Ala-Pro-Gln-Asp-Arg-; -Arg-Gly-Ala-Pro-Gln-Asp-Ser-; -Arg-Arg-Ala-Pro-Glu-Asp-Ser-; or -Arg-Arg-Ala-Ser-Gln-Asp-Ser- [SEQ ID NOS: 23 through 27, respectively]. As can be determined from review of the examples below, the inclusion of these optional immunogens into the primary composition can induce antibodies that react with rare Tat proteins of HIV-1 which are not cross-reactive with, or do not have a sufficiently strong cross-reactivity to, antibodies induced by the primary immunogens.

With regard to compositions of the invention which include optional immunogens, the composition may contain multiple peptides or polypeptides which contain multiple copies of a single optional immunogen sequence or multiple copies of different optional immunogen amino acid sequences in any order, or multiple copies of one or two of these optional sequences with some or all of the primary immunogens. In any variation, it is preferred for the efficacy of the primary composition, that at least one copy of all four primary amino acid sequences are present in the composition. It is not important for the function of the composition, whether the optional amino acid sequences are present in one or more peptides or polypeptides.

The amino acid sequences identified above may be flanked by other amino acids in the optional immunogen peptides or polypeptides; but the identity of the flanking amino acids is not essential to the biological function of the composition of this invention.

While the amino acid sequences useful in the primary immunogens and optional immunogens identified herein were obtained by rigorous analysis of over 400 known Tat sequences of HIV-1, it should be understood by one of skill in the art that similar compositions may be obtained using Tat proteins, the nucleic acid sequences encoding them, and fragments thereof from newly isolated Tat proteins of HIV-1 subtype B, or from Tat proteins of the other subtypes, or from other HIV strains.

Thus, the compositions of this invention, i.e., the peptide/polypeptides containing the above-identified amino acid sequences, when provided to a human subject, are useful in the immunologic interdiction of extracellular Tat proteins of most HIV-1 strains. These compositions function to critically reduce explosive multiplication of the virus and permit effective immune control of the virus.

The primary immunogens, with or without any optional immunogens may be presented in a variety of forms, for example, chemically synthesized or as recombinant peptides, polypeptides, proteins, fusion proteins or fused peptides. As pharmaceutical compositions, these primary compositions are admixed with a pharmaceutically acceptable vehicle, such as saline or phosphate buffered saline, suitable for administration as a protein composition for prophylaxis or treatment of virus infections. These proteins may be combined in a single pharmaceutical preparation for administration. Suitable adjuvants may also be employed in the protein-containing primary compositions of this invention.

As one embodiment, a composition of the present invention may be a synthetic peptide, containing single or multiple copies of the same or different primary immunogen amino acid sequences, and amino acid sequences of the optional immunogens, coupled to a selected carrier protein. In this embodiment of a composition of this invention, multiple different above-described primary and optional amino acid sequences with or without flanking sequences, may be combined sequentially in a polypeptide and coupled to the same carrier. Alternatively, the primary immunogens, and any optional immunogens may be coupled individually as peptides to the same or a different carrier, and the resulting immunogen-carrier constructs blended together to form a single composition.

For this embodiment, the carrier protein is desirably a protein or other molecule which can enhance the immunogenicity of the primary or optional immunogen. Such a carrier may be a larger molecule which has an adjuvanting effect. Exemplary conventional protein carriers include, without limitation, $E.$ $coli$ DnaK protein, galactokinase (galK, which catalyzes the first step of galactose metabolism in bacteria), ubiquitin, α-mating factor, β-galactosidase, and influenza NS-1 protein. Toxoids (i.e., the sequence which encodes the naturally occurring toxin, with sufficient modifications to eliminate its toxic activity) such as diphtheria toxoid and tetanus toxoid may also be employed as carriers. Similarly a variety of bacterial heat shock proteins, e.g., mycobacterial hsp-70 may be used. Glutathione reductase (GST) is another useful carrier. One of skill in the art can readily select an appropriate carrier.

In particularly desirable immunogen-carrier protein construct, one or more primary immunogen and optional immunogen peptides/polypeptides may be covalently linked to a mycobacterial $E.$ $coli$ heat shock protein 70 (hsp70) [K. Suzue et al, $J.$ $Immunol.$, 156:873 (1996)]. In another desirable embodiment, the composition is formed by covalently linking the immunogen-containing peptide or polypeptide sequences to diphtheria toxoid.

In yet another embodiment, the peptides or polypeptide primary immunogens and any selected optional immunogens may be in the form of a multiple antigenic peptide ("MAP", also referred to as an octameric lysine core peptide) construct. Such a construct may be designed employing the MAP system described by Tam, *Proc. Natl. Acad. Sci. USA*, 85:5409–5413 (1988). This system makes use of a core matrix of lysine residues onto which multiple copies of the same primary or optional immunogens of the invention are synthesized as described [D. Posnett et al., *J. Biol. Chem.*, 263(4):1719–1725 (1988); J. Tam, "Chemically Defined Synthetic Immunogens and Vaccines by the Multiple Antigen Peptide Approach", *Vaccine Research and Developments*, Vol. 1, ed. W. Koff and H. Six, pp. 51–87 (Marcel Deblau, Inc., New York 1992)]. Each MAP contains multiple copies of only one peptide. Therefore a primary composition of this invention can include a MAP in which the peptide or polypeptide primary immunogen attached to the lysine core contains one or sequential repeats of the four "primary" amino acid sequences identified above. Multiple different MAPs may be employed to obtain all four primary sequences and a selected number of optional immunogen sequences. Preferably these MAP constructs are associated with other T cell stimulatory sequences, or as pharmaceutical compositions, administered in conjunction with T cell stimulatory agents, such as known adjuvants.

In either of the above compositions, e.g., as peptide/polypeptide-carrier constructs or MAPs, each peptide/polypeptide immunogen, or each amino acid sequence in the immunogen, may be optionally separated by an optional amino acid sequences called "spacers". Spacers are sequences of between 1 to about 4 amino acids which are interposed between two sequences to permit linkage therebetween without adversely effecting the three dimensional structure of the immunogen. Spacers may also contain restriction endonuclease cleavage sites to enable separation of the sequences, where desired. Suitable spacers or linkers are known and may be readily designed and selected by one of skill in the art. Preferred spacers are sequences containing Gly or Ser amino acids.

B. Nucleic Acid Compositions of the Invention

Other embodiments of this invention include nucleic acid sequences, which encode the compositions, including the peptide and polypeptide immunogens of the compositions described above, including those peptides and polypeptides fused to carrier proteins. The nucleic acid sequences may also include sequences encoding the carrier proteins.

Thus, one preferred embodiment of the invention is a "synthetic gene" which encodes sequentially at least one or more copies of primary immunogen peptides/polypeptides comprising at least two of the amino acid sequences [SEQ ID NOS: 6 through 9, respectively]:

-Asp-Pro-Arg-Leu-Glu-Pro-;
-Asp-Pro-Lys-Leu-Glu-Pro-;
-Asp-Pro-Ser-Leu-Glu-Pro-; and
-Asp-Pro-Asn-Leu-Glu-Pro-.

As for the primary composition in protein/peptide form, the synthetic gene preferably encodes all four amino acid sequences of the primary immunogens. The synthetic gene can also encode any selection of the optional immunogens identified above. The synthetic gene may, as for the peptide/polypeptides described above, encode multiple copies of the same amino acid sequence, copies of multiple different immunogens or amino acid sequences, or multiple copies of multiple different immunogens or amino acid sequences. The synthetic gene may encode a desired peptide or polypeptide immunogen, or multiple peptide or polypeptide immunogens containing the selected amino acid sequences, which peptide/polypeptide is expressed in an open reading frame with, or fused to, a carrier protein. A further characteristic of the synthetic gene may be that it encodes a spacer between each immunogen or between each of the amino acid sequences in the immunogen, or between the immunogen and the carrier protein.

The synthetic gene of the present invention may also be part of a synthetic or recombinant molecule. The synthetic molecule may be a nucleic acid construct, such as a vector or plasmid which contains the synthetic gene encoding the protein, peptide, polypeptide, fusion protein or fusion peptide under the operative control of nucleic acid sequences encoding regulatory elements such as promoters, termination signals, and the like. Such synthetic molecules may be used to produce the polypeptide/peptide immunogen compositions recombinantly.

The synthetic gene or synthetic molecules can be prepared by the use of chemical synthesis methods or preferably, by recombinant techniques. For example, the synthetic gene or molecules may contain certain preference codons for the species of the indicated host cell.

The synthetic gene or molecules, preferably in the form of DNA, may be used in a variety of ways. For example, these synthetic nucleic acid sequences may be employed to express the peptide/polypeptides of the invention in vitro in a host cell culture. The expressed immunogens, after suitable purification, may then be incorporated into a pharmaceutical reagent or vaccine.

Alternatively, the synthetic gene or synthetic molecule of this invention may be administered directly into a mammalian, preferably human subject, as so-called 'naked DNA' to express the protein/peptide immunogen in vivo in a patient. See, e.g., J. Cohen, *Science*, 259:1691–1692 (Mar. 19, 1993); E. Fynan et al., *Proc. Natl. Acad. Sci., USA*, 90:11478–11482 (December 1993); and J. A. Wolff et al., *Biotechniques*, 11:474–485 (1991), all incorporated by reference herein. The synthetic molecule, e.g., a vector or plasmid, may be used for direct injection into the mammalian host. This results in expression of the protein by host cells and subsequent presentation to the immune system to induce antibody formation in vivo.

In still another aspect of the present invention, the synthetic genes or molecules of this invention may be incorporated into a non-pathogenic microorganism. The resulting microorganism, when administered to a mammalian host expresses and multiplies the expressed compositions of this invention in vivo to induced specific antibody formation. For example, non-pathogenic recombinant viruses or commensal bacterium which carry the compositions or synthetic genes of this invention and are useful for administration to a mammalian patient may be prepared by use of conventional methodology and selected from among known non-pathogenic microorganisms.

Among commensal bacterium which may be useful for exogenous delivery of the synthetic molecule to the patient, and/or for carrying the synthetic gene into the patient in vivo, include, for example, various strains of Streptococcus, e.g., *S. gordonii*, or *E. coli*, Bacillus, Streptomyces, and Saccharomyces.

Suitable non-pathogenic viruses which may be engineered to carry the synthetic gene into the cells of the host include poxviruses, such as vaccinia, adenovirus, canarypox, retroviruses and the like. A number of such non-pathogenic viruses are commonly used for human gene therapy, and as carrier for other vaccine agents, and are known and selectable by one of skill in the art.

C. Preparation or Manufacture of Compositions of the Invention

The compositions of the invention, and the individual polypeptides/peptides containing the primary and optional immunogens of this invention, the synthetic genes, and synthetic molecules of the invention, may be prepared conventionally by resort to known chemical synthesis techniques, such as described by Merrifield, *J. Amer. Chem. Soc.*, 85:2149–2154 (1963). Alternatively, the compositions of this invention may be prepared by known recombinant DNA techniques by cloning and expressing within a host microorganism or cell a DNA fragment carrying a sequence encoding a peptide/polypeptide containing a primary and/or optional immunogen and optional carrier protein. Coding sequences for the primary and optional immunogens can be prepared synthetically [W. P. C. Stemmer et al, *Gene*, 164:49 (1995) or can be derived from viral RNA by known techniques, or from available cDNA-containing plasmids.

Combinations of these techniques may be used, such as for production of the synthetic gene, which may require assembly of sequential immunogens by conventional molecular biology techniques, and site-directed mutagenesis to provide desired sequences of immunogens. The product of the synthetic gene is then produced recombinantly. All of these manipulations may be performed by conventional methodology.

Systems for cloning and expressing the peptide/polypeptide compositions of this invention using the synthetic genes or molecules, include various microorganisms and cells which are well known in recombinant technology. These include, for example, various strains of *E. coli*, Bacillus, Streptomyces, and Saccharomyces, as well as mammalian, yeast and insect cells. Suitable vectors therefor are known and available from private and public laboratories and depositories and from commercial vendors. Currently, the most preferred host is a mammalian cell such as Chinese Hamster ovary cells (CHO) or COS-1 cells. These hosts may be used in connection with poxvirus vectors, such as vaccinia or swinepox. The selection of other suitable host cells and methods for transformation, culture, amplification, screening and product production and purification can be performed by one of skill in the art by reference to known techniques. See, e.g., Gething and Sambrook, *Nature*, 293:620–625 (1981).

Another preferred system includes the baculovirus expression system and vectors.

When produced by conventional recombinant means, the compositions of this invention, i.e., the polypeptide/peptides containing the indicated copies of the primary immunogens and optional immunogens may be isolated either from the cellular contents by conventional lysis techniques or from cell medium by conventional methods, such as chromatography. See, e.g., Sambrook et al., *Molecular Cloning. A Laboratory Manual.*, 2d Edit., Cold Spring Harbor Laboratory, New York (1989).

Suitable plasmid and viral vectors used either for production of the peptide/polypeptide components as DNA vaccines are well known to those of skill in the art and are not a limitation of the present invention. See, Sambrook et al., cited above and the references above to production of the protein. See, also International Patent Application PCT WO94/01139, published Jan. 20, 1994.

Briefly, the DNA encoding the selected peptide/polypeptide is inserted into a vector or plasmid which contains other optional flanking sequences, a promoter, an mRNA leader sequence, an initiation site and other regulatory sequences capable of directing the multiplication and expression of that sequence in vivo or in vitro. These vectors permit infection of patient's cells and expression of the synthetic gene sequence in vivo or expression of it as a protein/peptide or fusion protein/peptide in vitro.

The resulting composition may be formulated into a primary composition with any number of optional immunogens and screened for efficacy by in vivo assays. Such assays employ immunization of an animal, e.g., a rabbit or a simian, with the composition, and evaluation of titers of antibody to the Tat proteins of HIV-1 or to synthetic detector peptides corresponding to variant Tat sequences (as shown in the examples below).

D. Antibody Compositions of the Invention

An isolated mammalian antibody composition which is directed against a peptide or polypeptide of the invention, as described above, is also an aspect of this invention. Such polyclonal antibody compositions are produced by immunizing a mammal with a peptide/polypeptide composition containing an assortment of primary immunogens and optional immunogens, as described above. Suitable mammals include primates, such as monkeys; smaller laboratory animals, such as rabbits and mice, as well as larger animals, such as horse, sheep, and cows. Such antibodies may also be produced in transgenic animals. However, a desirable host for raising polyclonal antibodies to a composition of this invention includes humans.

The polyclonal antibodies raised in the mammal exposed to the composition are isolated and purified from the plasma or serum of the immunized mammal by conventional techniques. Conventional harvesting techniques can include plasmapheresis, among others.

Such polyclonal antibody compositions may themselves be employed as pharmaceutical compositions of this invention. Alternatively, other forms of antibodies may be developed using conventional techniques, including monoclonal antibodies, chimeric antibodies, humanized antibodies and fully human antibodies. See, e.g., Harlow et al., *Antibodies A Laboratory Manual*, Cold Spring Harbor Laboratory, (1988); Queen et al., *Proc. Nat'l. Acad. Sci. USA*, 86:10029–10032 (1989); Hodgson et al., *Bio/Technology*, 9:421 (1991); International PCT Application PCT/GB91/01554, Publication No. WO92/04381 and International PCT Application PCT/GB93/00725, Publication No. WO93/20210]. Other anti-Tat antibodies may be developed by screening hybridomas or combinatorial libraries, or antibody phage displays [W. D. Huse et al., *Science*, 246:1275–1281 (1988)] using the polyclonal or monoclonal antibodies produced according to this invention and the amino acid sequences of the primary or optional immunogens.

These antibody compositions bind to most Tat protein variants of HIV-1, and prevent the Tat proteins from supporting further HIV-1 multiplication. Thus, these antibodies are useful in pharmaceutical methods and formulations described below.

E. Pharmaceutical Compositions of the Invention

As another aspect of this invention, a pharmaceutical composition useful for inducing antibodies that react with most HIV-1 Tat proteins and impair the multiplication of HIV-1 is provided. This composition can comprise as its active agents, one of the following above-described components:

(a) a peptide/polypeptide primary immunogen which contains at least two, and preferably all four of the primary amino acid sequences and optionally contains other optional immunogens. These primary/optional immunogens may be in the form of recombinant proteins. Alternatively, they may be in the form of a mixture of carrier protein conjugates or MAPs.

(b) a synthetic gene described above;
(c) a synthetic molecule described above;
(d) a recombinant virus carrying the synthetic gene or molecule; and
(e) a commensal bacterial carrying the synthetic gene or molecule. The selected active component(s) is present in a pharmaceutically acceptable carrier, and the composition may contain additional ingredients. All of these pharmaceutical compositions can operate to lower the viral levels of a mammal.

The peptide/polypeptide compositions and synthetic genes or molecules in vivo are capable of eliciting in an immunized host mammal, e.g., a human, an immune response capable of interdicting most extracellular Tat protein variants from HIV-1 and thereby lowering the viral levels.

Pharmaceutical formulations containing the compositions of this invention may contain other active agents, such as T cell stimulatory agents for the MAPs, adjuvants and immunostimulatory cytokines, such as IL-12 and other well-known cytokines, for the protein/peptide compositions.

Suitable pharmaceutically acceptable carriers for use in an immunogenic proteinaceous composition of the invention are well known to those of skill in the art. such carriers include, for example, saline, a selected adjuvant, such as aqueous suspensions of aluminum and magnesium hydroxides, liposomes, oil in water emulsions and others. The present invention is not limited by the selection of the carrier or adjuvant.

Yet another pharmaceutical composition useful for impairing the multiplication of HIV-1 comprises an antibody composition as described in detail above. In a pharmaceutical composition, the antibodies may be carried in a saline solution of other suitable carrier. The antibody compositions are capable of providing an immediate, exogenously provided interdiction of Tat.

The preparation of these pharmaceutically acceptable compositions, from the above-described components, having appropriate pH isotonicity, stability and other conventional characteristics is within the skill of the art.

F. Method of the Invention—Impairing Multiplication of HIV-1

According to the present invention, a method for reducing the viral levels of HIV-1 involves exposing a human to the Tat antibody-inducing pharmaceutical compositions described above, actively inducing antibodies that react with most HIV-1 Tat proteins, and impairing the multiplication of the virus in vivo. This method is appropriate for an HIV-1 infected subject with a competent immune system, or an uninfected or recently infected subject. The method induces antibodies which react with HIV-1 Tat proteins, which antibodies reduce viral multiplication during any initial acute infection with HIV-1 and minimize chronic viremia leading to AIDS. This method also lowers chronic viral multiplication in infected subjects, again minimizing progression to AIDS.

In one embodiment, the pharmaceutical compositions may be therapeutically administered to an HIV-1 infected human with a competent immune system for treatment or control of viral infection. Such an infected human may be asymptomatic. In a similar embodiment, the pharmaceutical compositions may be administered to an uninfected human for prophylaxis.

In these two instances, the pharmaceutical compositions preferably contain the peptide/polypeptide compositions, the synthetic genes or molecules, the recombinant virus or the commensal recombinant bacterium. Each of these active components of the pharmaceutical composition actively induces in the exposed human the formation of anti-Tat antibodies which block the transfer of Tat from infected cells to other infected or uninfected cells. This action reduces the multiplicity of infection and blocks the burst of HIV-1 viral expansion, and thus lowers viral levels. In already infected patients, this method of reduction of viral levels can reduce chronic viremia and progression to AIDS. In uninfected humans, this administration of the compositions of the invention can reduce acute infection and thus minimize chronic viremia leading to progression to AIDS.

Yet another aspect of the invention is a method for reducing the viral levels of HIV-1 by administering to a human, who is incapable of mounting an effective or rapid immune response to infection with HIV-1, a pharmaceutical composition containing the antibody compositions described above. The method can involve chronically administering the composition. Among such patients suitable for treatment with this method are HIV-1 infected patients who are immunocompromised by disease and unable to mount a strong immune response. In later stages of HIV infection, the likelihood of generating effective titers of antibodies is less, due to the immune impairment associated with the disease. Also among such patients are HIV-1 infected pregnant women, neonates of infected mothers, and unimmunized patients with putative exposure (e.g., a human who has been inadvertently "stuck" with a needle used by an HIV-1 infected human).

For such patients, the method of the invention preferably employs as the pharmaceutical composition the antibody composition of the invention, which is a polyclonal antibody composition prepared in other mammals, preferably normal humans. Alternatively, the other forms of antibody described above may be employed. These antibody compositions are administered as passive immunotherapy to inhibit viral multiplication and lower the viral load. The exogenous antibodies which react with most Tat proteins from HIV-1 provide in the patient an immediate interdiction of the transfer of Tat from virally infected cells to other infected or uninfected cells. According to this method, the patient may be chronically treated with the antibody composition for a long treatment regimen.

In each of the above-described methods, these compositions of the present invention are administered by an appropriate route, e.g., by the subcutaneous, oral, intravenous, intraperitoneal, intramuscular, rectal or vaginal routes. The presently preferred route of administration is intramuscular for the immunizing (active induction) compositions and intravenous or intramuscular for the antibody (passive therapy) compositions. The recombinant viral vectors and/or live commensal bacteria may be delivered orally.

The amount of the protein, peptide or nucleic acid sequences of the invention present in each vaccine dose is selected with regard to consideration of the patient's age, weight, sex, general physical condition and the like. The amount of active component required to induce an immune response, preferably a protective response, or produce an exogenous effect in the patient without significant adverse side effects varies depending upon the pharmaceutical composition employed and the optional presence of an adjuvant (for the protein-containing compositions).

Generally, for the compositions containing protein/peptide, fusion protein, MAP or coupled protein, or antibody composition, each dose will comprise between about 50 μg to about 1 mg of the peptide/polypeptide immunogens per mL of a sterile solution. A more preferred dosage may be about 200 μg of immunogen. Other dosage ranges may also be contemplated by one of skill in the art. Initial doses may be optionally followed by repeated boosts, where desirable.

The antibody compositions of the present invention can be employed in chronic treatments for subjects at risk of acute infection due to needle sticks or maternal infection. A dosage frequency for such "acute" infections may range from daily dosages to once or twice a week i.v. or i.m., for a duration of about 6 weeks. The antibody compositions of the present invention can also be employed in chronic treatments for infected patients, or patients with advanced HIV. In infected patients, the frequency of chronic administration may range from daily dosages to once or twice a week i.v. or i.m., and may depend upon the half-life of the immunogen (e.g., about 7–21 days). However, the duration of chronic treatment for such infected patients is anticipated to be an indefinite, but prolonged period.

Alternatively, compositions of this invention may be designed for direct administration of synthetic genes or molecules of this invention as "naked DNA". Suitable vehicles for direct DNA, plasmid nucleic acid, or recombinant vector administration include, without limitation, saline, or sucrose, protamine, polybrene, polylysine, polycations, proteins, $CaPO_4$ or spermidine. See e.g, PCT application WO94/01139 and the references cited above. As with the protein immunogenic compositions, the amounts of components in the DNA and vector compositions and the mode of administration, e.g., injection or intranasal, may be selected and adjusted by one of skill in the art. Generally, each dose will comprise between about 50 μg to about 1 mg of immunogen-encoding DNA per mL of a sterile solution.

For recombinant viruses containing the synthetic genes or molecules, the doses may range from about 20 to about 50 ml of saline solution containing concentrations of from about $1\times10^7$ to $1\times10^{10}$ pfu/ml recombinant virus of the present invention. A preferred human dosage is about 20 ml saline solution at the above concentrations. However, it is understood that one of skill in the art may alter such dosages depending upon the identity of the recombinant virus and the make-up of the immunogen that it is delivering to the host.

The amounts of the commensal bacteria carrying the synthetic gene or molecules to be delivered to the patient will generally range between about $10^3$ to about $10^{12}$ cells/kg. These dosages, will of course, be altered by one of skill in the art depending upon the bacterium being used and the particular composition containing primary and optional immunogens being delivered by the live bacterium.

Thus, the compositions of this invention are designed to retard or minimize infection by the selected virus of an uninfected mammal, e.g., human. Such compositions thus have utility as vaccines. Anti-Tat protein antibodies are not reactive with the HIV-1 proteins used in diagnostic assays to detect seroconversion after infection. Thus, subjects treated with the compositions of this invention would not be stigmatized with false-positive tests for HIV-1 infection, and it would remain possible to detect seroconversion if treated subjects did become infected with HIV-1.

Providing a mammal with the compositions of this invention, whether as a protein/peptide-containing composition or by administration of a novel nucleic acid sequence encoding the immunogen, affords a radically different strategy for AIDS vaccination because it permits the lowering of viral levels by biological interdiction of most known Tat protein variants of HIV-1, lowering multiplication of HIV-1.

The use of the Tat immunogen-containing compositions has a particularly desirable advantage in contrast to other treatments and prophylactic methods employed against such viruses. Because interdiction of the Tat protein extracellularly inhibits the multiplication of all HIV quasi-species or strains indiscriminately, it does not create a selective pressure on the parent virus itself for selection of mutant virus variants. Thus, blocking the uptake of Tat protein by the patient's cells not only reduces the level of viremia, but does so in a manner that precludes the selection of "escape variants".

Additionally, the invention comprises a method of actively treating asymptomatic HIV-1 infected subjects with viremia, since during the course of the disease, extracellular Tat protein likely contributes to the persistent infection and immune abnormalities that are present at this stage of HIV-1 infection. Interdiction of extracellular Tat protein by antibodies induced by immunization according to this invention can reduce viremia with more effective immune control, and result in delay or prevention of progression to AIDS.

The mechanism of the present invention as described above is useful in impeding the course of viral infection and producing desirable clinical results. More specifically, the compositions of this invention are capable of reducing viremia in patients already infected with the virus by blocking further uptake of the Tat protein by uninfected cells. The compositions of the present invention, used either alone or in conjunction with other therapeutic regimens for HIV infected patients, are anticipated to assist in the reduction of viremia and prevention of clinical deterioration.

For such therapeutic uses, the formulations and modes of administration are substantially identical to those described specifically above and may be administered concurrently or simultaneously with other conventional therapeutics for the specific viral infection. For therapeutic use or prophylactic use, repeated dosages of the immunizing compositions may be desirable, such as a yearly booster or a booster at other intervals.

G. Advantages of the Invention

One of the advantages of the compositions of this invention is the small number of immunogens required for inclusion into a composition of this invention to cross-react with greater than 97% of known Tat protein variants of HIV-1 of the common B subtype. As illustrated in the examples below, the primary immunogenic composition containing all four primary amino acid sequences cross-reacts with 387 of 399 Tat proteins of HIV-1 of the common B subtype, as well as with all 18 Tat protein sequences from less frequent non-B subtypes of HIV-1. Thus, a single composition may be usefully employed in protecting against or treating infection, caused by the vast majority of HIV-1 strains that can be encountered.

Further, having identified the precise epitopes on Tat against which binding is desired (i.e., AA5-10 or AA56-62 of SEQ ID NO: 1) new desirable Tat peptide immunogens from newly occurring HIV-1 strains or newly discovered strains may be easily identified using the methods described herein, and included in the compositions. This flexibility enables the compositions of this invention to be useful prophylactically against any new strain or strains of HIV-1 identified in the future. In view of the teachings herein, one of skill in the art is expected to be readily able to incorporate new combinations of Tat immunogens (and the nucleic acid constructs encoding them) into the compositions.

For example, the use of conventional techniques such as PCR and high density oligonucleotide arrays [M. J. Kozal et al, *Nature Med.*, 2:753 (1996)] enables one of skill in the art to obtain the amino acid sequences of a large array of HIV-1 Tat proteins representing variants of clinical isolates of HIV-1 strains and subtypes. Using such techniques permits determination of other variants of the HIV-1 B subtype as well as other subtypes in undeveloped countries, which have not been so intensively studied to date. The determination of new Tat sequences will enable ready inclusion of the corresponding peptides as immunogens into compositions of this invention, allowing the induction of an antibody response against other rare Tat proteins of HIV-1.

Cross-reactivity studies with antibodies raised to synthetic peptides corresponding to each Tat variant can be utilized to eliminate the need for immunizing with Tat variants in which the sequence changes are immunologically silent, in that these peptides are strongly bound by antibodies to the consensus sequence or other variants.

The following examples illustrate preferred methods for preparing the compositions of the invention and utilizing these compositions to induce antibodies to Tat proteins of the virus in an immunized host. These examples are illustrative only and do not limit the scope of the invention.

EXAMPLE 1
IMMUNOLOGICAL STUDIES ON MINIMAL TAT PROTEIN AMINO ACID SEQUENCES NECESSARY FOR BINDING TO ANTIBODY FOR TWO B CELL EPITOPES IN HIV-1 TAT PROTEIN

Two peptides were synthesized as described below, and these corresponded to amino acids 4–16 and 53–62 of SEQ ID NO: 1 illustrated in FIG. 1. The sequences are the most frequent sequence representations at these positions in 31 Tat protein sequences of the common B subtype reported in the NIAID HIV database. The sequences were chosen as putative immunogens.

A. Peptide synthesis—immunizing peptides

The two immunogens, amino acid sequences -Val-Asp-Pro-Arg-Leu-Glu-Pro-Trp-Lys-His-Pro-Gly-Ser- [SEQ ID NO: 28] and -Arg-Gln-Arg-Arg-Arg-Ala-Pro-Gln-Asp-Ser- [SEQ ID NO: 29], respectively, were synthesized by solid phase methodology on polypropylene pegs according to the methods of H. M. Geysen et al., *J. Immunol. Meth.*, 102:259 (1987), with an N-terminal cysteinyl being incorporated to facilitate coupling to a carrier protein. The N-terminus was left as a free amine and the C-terminus was amidated.

Immunizing peptides were generally purified to greater than 95% purity by reverse phase HPLC, and purity was further confirmed by mass spectometry (MS).

Immunizing peptides were covalently coupled to diphtheria toxoid (DT) carrier protein via the cysteinyl side chain by the method of A. C. J. Lee et al., *Molec. Immunol.*, 17:749 (1980), using a ratio of 6–8 moles peptide per mole of diphtheria toxoid.

B. Peptide synthesis—Detector peptides

Peptides corresponding to the amino acid sequences of the two immunogen peptides were synthesized by the method of Geysen, cited above, for use in ELISA assays for detection of reactivity and cross-reactivity. Additional peptides with N- and C-terminal truncations were also synthesized.

Detector peptides had an N-terminal -Ser-Gly-Ser-Gly- [SEQ ID NO: 30] added, with biotinylation of the new N-terminus, and the C-terminal remained a free acid. These detector peptides had a purity exceeding 70% by mass spectometry and were not purified further.

C. Immunization of rabbits

The peptide conjugates were taken up in purified water and emulsified 1:1 with complete Freund's adjuvant (CFA) or incomplete Freund's adjuvant (IFA) [ANTIBODIES—A LABORATORY MANUAL, Eds. E. Harlow and P. Lane, Cold Spring Harbor Laboratory (1998)]. Total volume per rabbit was 1 ml, and this contained 100 µg of peptide coupled to DT.

Two rabbits were used for each immunizing peptide, with the initial intramuscular (IM) injection with conjugate in CFA and a subsequent IM boost at 2 weeks with conjugate in IFA. A pre-bleed was drawn before the first injection and larger bleeds were taken 3 and 5 weeks after the booster injection.

D. ELISA determination of binding of antiserums to biotinylated peptides

These assays were performed as described by H. M. Geysen et al., *Proc. Natl. Acad. Sci. USA*, 81:3998 (1983). Briefly, using Nunc Immuno Maxisorb™ 96 well plates, biotinylated peptides were bound to streptaviden coated plates and, with washing with phosphate buffered saline (PBS) between steps, successive incubations were performed with antiserum dilutions and horseradish peroxidase conjugated anti-rabbit immunoglobulin to detect bound antibody. Plated were developed with ABTS, with an O.D. reading at 405 nm. Absorbance greater than O.D. 1.0 was taken as positive and titers were determined from doubling dilutions of each antiserum. The geometric mean titer (GMT) was calculated for each antiserum pair for a given immunogen.

E. Determination of antibody binding sequences

ELISA results demonstrated that the antibodies to the first immunogen were reacting with the sequence -Asp-Pro-Arg-Leu-Glu-Pro [AA 5-10 of SEQ ID NO: 1] and that antibodies to the second immunogen were reacting with the sequence -Arg-Arg-Ala-Pro-Gln-Asp-Ser-[AA 56-62 of SEQ ID NO: 1]. N- or C-terminal truncation of these sequences reduced the ELISA titer, so these hexapeptide and heptapeptide sequences constituted the antibody binding region and were termed HIV-1 Tat protein B cell epitope 1 and epitope 2, respectively. These results are summarized in Tables 1 and 2 below. From the results of Table 1, the minimal epitope 1 was -Asp-Pro-Arg-Leu-Glu-Pro- [SEQ ID NO: 6]. From the results of Table 2, the minimal epitope 2 was -Arg-Arg-Ala-Pro-Gln-Asp-Ser- [SEQ ID NO: 19].

TABLE 1

| Detector Sequence* | Antiserum to: -Val-Asp-Pro-Arg-Leu-Glu-Pro-Trp-Lys-His-Pro-Gly-Ser-; GMT (% binding versus immunogen) | SEQ ID NO |
|---|---|---|
| -Val-Asp-Pro-Arg-Leu-Glu-Pro-Trp-Lys-His-Pro-Gly-Ser- | 65,885 (100) | 28/31 |
| -Asp-Pro-Arg-Leu-Glu-Pro-Trp-Lys-His-Pro-Gly-Ser- | 83,753 (127) | 32 |
| -Val-Asp-Pro-Arg-Leu-Glu-Pro-Trp | 96,627 (147) | 33 |

TABLE 1-continued

| Detector Sequence* | Antiserum to: -Val-Asp-Pro-Arg-Leu-Glu-Pro-Trp-Lys-His-Pro-Gly-Ser-; GMT (% binding versus immunogen) | SEQ ID NO |
|---|---|---|
| -Val-Asp-Pro-Arg-Leu-Glu-Glu-Pro- | 80,960 (123) | 34 |
| -Val-Asp-Pro-Arg-Leu-Glu | 32,016 (49) | 35 |

*Substitution of Asp to Gly, Ala or His reduced titer to <1% (See Example 2)

TABLE 2

| Detector Sequence | Antiserum to: -Arg-Gln-Arg-Arg-Arg-Ala-Pro-Gln-Asp-Ser; GMT (% binding) versus immunogen) | SEQ ID NO |
|---|---|---|
| -Arg-Gln-Arg-Arg-Arg-Ala-Pro-Gln-Asp-Ser- | 34,305 (100) | 29 |
| -Gln-Arg-Arg-Arg-Ala-Pro-Gln-Asp-Ser- | 32,119 (91) | 36 |
| -Arg-Arg-Arg-Ala-Pro-Gln-Asp-Ser- | 32,029 (91) | 37 |
| -Arg-Arg-Ala-Pro-Gln-Asp-Ser- | 36,165 (102) | 19 |
| -Arg-Ala-Pro-Gln-Asp-Ser- | 10,357 (29) | 38 |
| -Arg-Gln-Arg-Arg-Arg-Ala-Pro-Gln-Asp- | 2,440 (7) | 39 |
| -Arg-Gln-Arg-Arg-Arg-Ala-Pro-Gln- | 704 (2) | 40 |

EXAMPLE 2
SEQUENCE VARIATIONS IN EPITOPE 1 OF HIV-1 TAT PROTEIN AND IMMUNOLOGICAL CROSS-REACTIVITIES OF ANTISERUMS TO THESE SEQUENCES

Variations in the sequence of Tat protein AA 5-10 of SEQ ID NO: 1 were analyzed in sequences available in HUMAN RETROVIRUSES and AIDS 1996, published by the Theoretical Biology and Biophysics Group of the Los Alamos National Laboratory, Los Alamos, N.Mex., and additional sequences kindly obtained from GenBank by Esther Guzman of the Los Alamos Laboratory.

A. Variations in sequences 399 aa 5-10 Tat hexapeptide sequences of the common B subtype of HIV-1 were obtained, as were 18 from the non-B subtypes (6 from subtype A, 2 from subtype C, 7 from subtype D, 2 from subtype F and 1 from subtype U).

For the B subtype, 386 of the total 399 (97%) hexapeptides had either Arg (289, 74%), or Lys (45, 11%), or Ser (36, 9%) or Asn (16, 4%) in position 3 as the only variation in the hexapeptides. The remaining variations (3%) comprised:

-Gly-Pro-Arg-Leu-Glu-Pro-(4) [SEQ ID NO: 11],
-Asp-Pro-Gly-Leu-Glu-Pro-(2) [SEQ ID NO: 14], and single examples of:
    -Asp-His-Arg-Leu-Glu-Pro- [SEQ ID NO: 41],
    -Ala-Pro-Arg-Leu-Glu-Pro- [SEQ ID NO: 12],
    -His-Pro-Arg-Leu-Glu-Pro- [SEQ ID NO: 13],
    -Asp-Pro-Arg-Ile-Glu-Pro- [SEQ ID NO: 15],
    -Asp-Pro-Arg-Leu-Gly-Pro- [SEQ ID NO: 16],
    -Asp-Pro-Arg-Leu-Glu-Ala- [SEQ ID NO: 17] and
-Asn-Pro-Ser-Leu-Glu-Pro- [SEQ ID NO: 18].

For the 18 non-B subtype sequences, 2 had Arg, 1 had Lys, 2 had Ser and 9 had Asn at position 3 of the hexapeptides aa5-10, and other variants were
-Asp-Pro-Asn-Leu-Asp-Pro-(2) [SEQ ID NO: 42] and single examples of
-Asp-Pro-Asn-Ile-Glu-Pro- [SEQ ID NO: 43] and
-Asp-Pro-Asn-Leu-Glu-Ser- [SEQ ID NO: 44].

B. Assessment of immunological reactivity and cross-reactivity of the four primary immunogens Immunizing and detector sequences were synthesized, as described in Example 1, for the following sequences [SEQ ID NOS: 28 and 45 through 47, respectively]:
-Val-Asp-Pro-Arg-Leu-Glu-Pro-Trp-Lys-His-Pro-Gly-Ser-,
-Val-Asp-Pro-LYs-Leu-Glu-Pro-Trp-Lys-His-Pro-Gly-Ser-,
-Val-Asp-Pro-Ser-Leu-Glu-Pro-Trp-Lys-His-Pro-Gly-Ser-,
-Val-Asp-Pro-Asn-Leu-Glu-Pro-Trp-Lys-His-Pro-Gly-Ser-.

Rabbits were immunized and the antiserums were tested by ELISA, as described in Example 1, for reactivity and cross-reactivity. Self-reactivities are summarized in Table 3.

TABLE 3

| Immunogen and detector sequence | GMT | SEQ ID NO |
|---|---|---|
| —Val—Asp—Pro—Arg—Leu—Glu—Pro—Trp—Lys—His—Pro—Gly—Ser— | 88,000 | 28 |
| —Val—Asp—Pro—Lys—Leu—Glu—Pro—Trp—Lys—His—Pro—Gly—Ser— | 132,000 | 45 |
| —Val—Asp—Pro—Ser—Leu—Glu—Pro—Trp—Lys—His—Pro—Gly—Ser— | 166,355 | 46 |
| —Val—Asp—Pro—Asn—Leu—Glu—Pro—Trp—Lys—His—Pro—Gly—Ser— | 173,097 | 47 |

Cross-reactivities between these primary immunogens are displayed in Table 4.

TABLE 4

| | Antiserums to primary immunogens (figures denote % reactivity v. self-reactivity) | | | |
|---|---|---|---|---|
| Detectors | Arg3 | Lys3 | Ser3 | Asn3 |
| Arg3 | 100 | 49 | 3 | 4 |
| Lys3 | 24 | 100 | 6 | 5 |

TABLE 4-continued

| | Antiserums to primary immunogens (figures denote % reactivity v. self-reactivity) | | | |
|---|---|---|---|---|
| Detectors | Arg3 | Lys3 | Ser3 | Asn3 |
| Ser3 | 11 | 16 | 100 | 15 |
| Asn3 | 11 | 22 | 10 | 100 |

Tables 3 and 4 demonstrate that each variant is an effective immunogen, but in general there is only modest cross-reactivity between variants. This implies that optimal coverage would require inclusion of all four variants as immunogens in a primary composition as described above.

C. Assessment of cross-reactivities of other variants.

Detector peptides were made for all remaining epitope variants and tested for cross-reactivity with the antiserums to the appropriate position 3 primary hexapeptide immunogen. The cross-reactivities versus self-reactivity with the appropriate position 3 primary immunogen are displayed in Table 5.

TABLE 5

| Detector sequence (variations in epitope 1) | % cross-reactivity | SEQ ID NO |
|---|---|---|
| Cross-reactive | | |
| —Asp—His—Arg—Leu—Glu—Pro— | 55 | 41 |
| —Asp—Pro—Asn—Ile—Glu—Pro— | 70 | 43 |
| —Asp—Pro—Asn—Leu—Asp—Pro— | 100 | 42 |
| —Asp—Pro—Asn—Leu—Glu—Ser— | 78 | 44 |
| Non cross-reactive | | |
| —Gly—Pro—Arg—Leu—Glu—Pro— | 1 | 11 |
| —Ala—Pro—Arg—Leu—Glu—Pro— | 1 | 12 |
| —His—Pro—Arg—Leu—Glu—Pro— | 1 | 13 |
| —Asp—Pro—Gly—Leu—Glu—Pro— | 1 | 14 |
| —Asp—Pro—Arg—Ile—Glu—Pro— | 9 | 15 |
| —Asp—Pro—Arg—Leu—Gly—Pro— | 10 | 16 |
| —Asp—Pro—Arg—Leu—Glu—Ala— | 1 | 17 |
| —Asn—Pro—Ser—Leu—Glu—Pro— | 10 | 18 |

The results of Tables 3–5 indicates that immunization with the four primary immunogens would generate antibodies reactive with greater than 97% of HIV-1 Tat proteins of the common B subtype. Interestingly all 18 non-B subtypes in the databases had epitope 1 sequences reactive with antibodies to the primary immunogens.

D. Immunogenicity of certain epitope 1 variants

Immunizing and detecting peptides were synthesized for the following 2 variant epitope 1 peptides, with immunizations and ELISA testing as in Example 1. The self titers (GMT) are displayed in Table 6.

TABLE 6

| Detecting and Immunizing Peptides | Self-titer (GMT) | SEQ ID NO |
|---|---|---|
| —Val—Asn—Pro—Ser—Leu—Glu—Pro—Trp—Lys—His—Pro—Gly—Ser— | 94,919 | 48 |
| —Val—Asp—His—Arg—Leu—Glu—Pro—Trp—Lys—His—Pro—Gly—Ser— | 72,686 | 49 |

These data show that inclusion of rare variants along with the primary immunogens expands antibody coverage to such rare epitope variants.

Immunization with the four primary epitope 1 sequences can induce high titer antibodies reactive with Tat proteins of >97% of all HIV-1 strains. This coverage can be optionally extended with the inclusion of additional rare epitope 1 variant sequences in the immunizing composition.

EXAMPLE 3

SEQUENCE VARIATIONS IN EPITOPE 2 OF HIV-1 Tat PROTEIN AND IMMUNOLOGICAL CROSS-REACTIVITIES OF ANTISERUMS TO THESE SEQUENCES

Variations in the sequence of Tat protein AA 56-72 were analyzed in sequences available in HUMAN RETROVIRUSES and AIDS 1996, published by the Theoretical Biology and Biophysics Group of the Los Alamos National Laboratory, Los Alamos, N.Mex., and additional sequences kindly obtained from GenBank by Esther Guzman of the Los Alamos Laboratory.

A. Variations in epitope 2 sequences 482 sequences of epitope 2 of the common B subtype of HIV-1 were available for analysis. The most frequent sequence found conformed to the formula -Arg-Arg-X-Pro-Gln-Y-Ser- [SEQ ID NO: 10], where X is Ala, Pro, Ser, or Gln, and Y is Asp, Asn, Gly or Ser. This sequence type, which appears immunologically cross-reactive (see below), was found in 292 of 482 (61%) of available Tat sequences.

Other sequence variants occurred in lower incidence and these included:

-Arg-Arg-Ala-Pro-Pro-Asp-Ser- (20, 4%) [SEQ ID NO: 20],
-Arg-Arg-Ala-Pro-Pro-Asp-Asn- (21, 4%) [SEQ ID NO: 50],
-Arg-Arg-Ala-His-Gln-Asp-Ser- (20, 4%) [SEQ ID NO: 21],
-Arg-Arg-Ala-His-Gln-Asn-Ser- (17, 3.5%) [SEQ ID NO: 22],
-Arg-Arg-Ala-Pro-Gln-Gly-Asn- (10, 2%) [SEQ ID NO: 51],
-Arg-Gly-Ala-Pro-Gln-Asp-Ser- (9, 2%) [SEQ ID NO: 25],
-Arg-Arg-Ala-Pro-Glu-Asp-Ser- (8, 2%) [SEQ ID NO: 26],
-Arg-Arg-Ala-Ser-Gln-Asp-Ser- (8, 2%) [SEQ ID NO: 27],
-Arg-Arg-Pro-Pro-Gln-Asp-Asn- (9, 2%) [SEQ ID NO: 23], and
-Arg-Arg-Ala-Pro-Gln-Asp-Arg- (8, 2%) [SEQ ID NO: 24].

Together these sequences account for 85% of epitope 2 variants, with the balance comprised of a large number of low incidence variations.

Epitope 2 sequences were only available from 18 examples of HIV-1 non-B subtypes. Unlike epitope 1, they showed divergence from the B subtype sequences and optionally a larger number of sequences can be selected for inclusion into the composition of this invention, if additional non-B subtype epitope 2 sequences are determined and are desirable in an immunogenic composition of this invention.

B. Assessment of immunological reactivity and cross reactivity of selected epitope 2 sequences Immunizing and detector sequences were synthesized, as described in Example 1, for the following sequences:

-Arg-Gln-Arg-Arg-Arg-Ala-Pro-Gln-Asp-Ser- [SEQ ID NO: 29],
-Arg-Gln-Arg-Arg-Arg-Ala-His-Gln-Asn-Ser- [SEQ ID NO: 52],
-Arg-Gln-Arg-Arg-Arg-Pro-Pro-Gln-Asp-Ser- [SEQ ID NO: 53],
-Gly-Arg-Gln-Arg-Arg-Arg-Ala-Pro-Gln-Asp-Ser- [SEQ ID NO: 54],
-Gly-Arg-Arg-Ala-His-Gln-Asp-Ser-Gly- [SEQ ID NO: 55],
-Gly-Arg-Arg-Ala-Pro-Pro-Asn-Ser-Gly- [SEQ ID NO: 56],

-Gly-Arg-Arg-Ala-Pro-Pro-Asp-Ser-Gly- [SEQ ID NO: 57], and -Arg-Arg-Ala-Pro-Gln-Asp-Ser-Gln-Thr-His-Gln- [SEQ ID NO: 58].

Rabbits were immunized and antiserums were tested by ELISA, as described in Example 1, for reactivity and cross-reactivity.

Additional detector peptides were synthesized as follows:

-Arg-Gln-Arg-Arg-Arg-Ala-Pro-Glu-Asp-Ser- [SEQ ID NO: 83],

-Arg-Gln-Arg-Arg-Arg-Pro-Pro-Gln-Gly-Ser- [SEQ ID NO: 59],

-Arg-Gln-Arg-Arg-Gly-Pro-Pro-Gln-Gly-Ser- [SEQ ID NO: 60],

-Arg-Gln-Arg-Arg-Arg-Pro-Pro-Gln-Asn-Ser- [SEQ ID NO: 61],

-Arg-Gln-Arg-Arg-Arg-Ser-Pro-Gln-Asp-Ser- [SEQ ID NO: 62],

-Arg-Gln-Arg-Arg-Arg-Ser-Pro-Gln-Asn-Ser- [SEQ ID NO: 63],

-Arg-Gln-Arg-Arg-Arg-Thr-Pro-Gln-Ser-Ser- [SEQ ID NO: 64],

-Arg-Gln-Arg-Arg-Arg-Ala-His-Gln-Asp-Ser- [SEQ ID NO: 65],

-Arg-Gln-Arg-Arg-Arg-Ala-Pro-Pro-Asp-Ser- [SEQ ID NO: 66],

-Arg-Arg-Ala-Pro-Pro-Asp-Asn- [SEQ ID NO: 50],
-Arg-Arg-Ala-Pro-Gln-Asp-Arg- [SEQ ID NO: 24],
-Arg-Arg-Ala-Pro-Gln-Asp-Asn- [SEQ ID NO: 67],
-Arg-Arg-Ala-Pro-Gln-Gly-Asn- [SEQ ID NO: 51],
-Arg-Arg-Thr-Pro-Gln-Gly-Ser- [SEQ ID NO: 68],
-Arg-Arg-Ala-Pro-Gln-Gly-Ser- [SEQ ID NO: 69],
-Arg-Arg-Thr-Pro-Gln-Asp-Ser- [SEQ ID NO: 70],
-Arg-Arg-Pro-Pro-Gln-Ser-Ser- [SEQ ID NO: 71],
-Arg-Arg-Ala-Pro-Gln-Asn-Ser- [SEQ ID NO: 72], and
-Arg-Arg-Ser-Pro-Gln-Asp-Ser- [SEQ ID NO: 73].

The various antiserums and detector peptides were utilized to determine immunogenicity of the various sequences and the extent of immunological cross reactivity.

The incidence and immunological reactivity of epitope 2 sequences of the formula -Arg-Arg-X-Pro-Gln-Y-Ser- [SEQ ID NO: 10] (see above) are shown in Table 7. In the Table 7 below, percent cross-reactivity was measured with antiserum to Cys-Arg-Gln-Arg-Arg-Arg-Ala-Pro-Gln-Asp-Ser- [SEQ ID NO: 74], self titer=46,115. The results of Table 7 below demonstrate that immunization with -Arg-Gln-Arg-Arg-Arg-Ala-Pro-Gln-Asp-Ser- [SEQ ID NO: 29] should provide effective cross-reactivity with most of these variants, represented in 61% of HIV-1 strains.

TABLE 7

| Epitope 2 sequence | Incidence in 482 sequences | % Cross-reactivity | SEQ ID NO |
|---|---|---|---|
| -Arg-Arg-Ala-Pro-Gln-Asp-Ser- | 93 | 100 | 19 |
| -Arg-Arg-Pro-Pro-Gln-Asp-Ser- | 50 | 111 | 75 |
| -Arg-Arg-Pro-Pro-Gln-Asn-Ser- | 41 | 96 | 76 |
| -Arg-Arg-Pro-Pro-Gln-Gly-Ser- | 37 | 97 | 77 |
| -Arg-Arg-Ser-Pro-Gln-Asp-Ser- | 19 | 93 | 73 |
| -Arg-Arg-Thr-Pro-Gln-Gly-Ser- | 14 | 56 | 68 |
| -Arg-Arg-Ala-Pro-Gln-Gly-Ser- | 9 | 87 | 69 |
| -Arg-Arg-Thr-Pro-Gln-Asp-Ser- | 7 | 116 | 70 |
| -Arg-Arg-Ala-Pro-Gln-Asn-Ser- | 5 | 128 | 72 |
| -Arg-Arg-Ser-Pro-Gln-Asp-Ser- | 4 | 110 | 73 |
| -Arg-Arg-Ser-Pro-Gln-Asn-Ser- | 2 | 142 | 78 |
| -Arg-Arg-Ala-Pro-Gln-Ser-Ser- | 1 | 97 | 79 |
| -Arg-Arg-Ser-Pro-Gln-Gly-Ser- | 1 | 78 | 80 |
| -Arg-Arg-Thr-Pro-Gln-Asn-Ser- | 1 | 43 | 81 |
| 292/482(61%) | | | |

Immunization with -Arg-Arg-Ala-Pro-Pro-Asp-Asn- [SEQ ID NO: 50] and -Arg-Arg-Ala-Pro-Pro-Asp-Ser- [SEQ ID NO: 20] yielded antibodies that cross-reacted with both detector peptides, as shown in Table 8. Thus, inclusion of either sequence in an immunizing composition of this invention would provide antibodies against Tat protein epitope 2 variants in a further 41/482 (8.5%) of HIV-1 strains.

Immunization with -Arg-Gln-Arg-Arg-Arg-Ala-His-Gln-Asn-Ser- [SEQ ID NO: 52] induced antibodies that gave a self titer of 209,286 and a cross-reactivity of 5,356 (2.5%) with -Arg-Arg-Ala-His-Gln-Asp-Ser- [SEQ ID NO: 21]. Thus inclusion of this sequence in an immunogen would cover an additional 17/482 (3.5%) of HIV-1 strains.

Thus, immunization with three epitope 2 variants,

-Arg-Arg-Ala-Pro-Gln-Asp-Ser- [SEQ ID NO: 19],

-Arg-Arg-Ala-Pro-Pro-Asp-Asn- [SEQ ID NO: 50], and

-Arg-Arg-Ala-His-Gln-Asn-Ser- [SEQ ID NO: 22], could provide antibodies reactive with the Tat proteins of 73% of HIV-1 strains.

TABLE 8

| | Detector peptides ELISA GMT | |
|---|---|---|
| Antiserum to: | -Arg-Arg-Ala-Pro-Pro-Asp-Asn- [SEQ ID NO: 50] | -Arg-Arg-Ala-Pro-Pro-Asp-Ser- [SEQ ID NO: 20] |
| -Arg-Arg-Ala-Pro-Pro-Asp-Asn- [SEQ ID NO: 50] | 11,056 | 12,230 |
| -Arg-Arg-Ala-Pro-Pro-Asp-Ser- [SEQ ID NO: 20] | 9,340 | 7,865 |

EXAMPLE 4

CONSTRUCTION OF A SYNTHETIC GENE OF THE INVENTION

A synthetic gene was constructed that incorporated in frame eight epitope 1 variants (including the four primary immunogens of the invention) and thirteen epitope 2 variants, these constituting all the variant epitope 1 and epitope 2 sequences found in the Tat protein sequences of 31

HIV-1 B subtype strains reported in the 1996 HUMAN RETROVIRUSES and AIDS compilation, published by the Theoretical Biology and Biophysics Group of the Los Alamos National Laboratory, Los Alamos, N.Mex. These included amino acids 4–16 for epitope 1 and 53–62 for epitope 2, using the numbering of SEQ ID NO: 1 illustrated in FIG. 1. The epitope sequences were separated by dipeptide spacers containing Gly and/or Ser residues.

The sequence of this one exemplary gene of this invention is shown in FIGS. 2A–2C [SEQ ID NOS: 2 and 3]. The gene was assembled as described in W. P. C. Stemmer et al., *Gene*, 164:49 (1995). Briefly, eleven top strand 60-mer oligonucleotides (oligos) and eleven bottom strand oligos with 20 nucleotide (nt) overlaps were synthesized along with two end 50-mers. The twenty-two 60-mers were incubated together under hybridizing conditions and polymerase chain reaction (PCR) was used to fill in the sequence and amplify it. The end 50-mers were then added and the assembly completed by PCR, with isolation of the full length gene on agarose gel.

The gene was sequenced and found to have the correct sequence within the actual epitopes, with the exception of an Ala to Thr substitution at position 136 (see FIGS. 2A–2C). This was accepted since this change does not affect antibody binding of epitope 2 (see Example 3).

This gene was then excised with restriction enzymes and inserted into the expression vector pBAD [L-M. Guzman et al., *J. Bacteriol*, 177:4121 (1950)] containing, in frame, the sequence for green fluorescent protein (GFP) [A. Crameri et al., *Nature Biotech*, 14:315 (1996)]. TG1 *E coli* were transfected and green-fluorescent colonies were isolated.

The isolated colonies were grown and expression was induced. Protein from each of three colonies had fluorescent bands on Western blotting with the expected molecular size (i.e., twice that of GFP alone). The resulting protein was soluble and was purified by nickel column affinity purification utilizing a hexa-histidyl that had been incorporated in the sequence.

Yield was approximately 1 mg protein per liter of supernatant after double affinity purification to yield >90% purity.

EXAMPLE 5
IMMUNOLOGICAL CHARACTERIZATION OF THE RECOMBINANT FUSION PROTEIN EXPRESSING HIV-1 Tat PROTEIN EPITOPE VARIANTS

A. Reactivity of fusion protein with rabbit antiserums to Epitope 1 and 2 variants.

Rabbit antiserums generated to synthetic peptides corresponding to the four primary epitope 1 sequences (see Example 2 and below) and four epitope 2 sequences (see below) were tested by ELISA, using the methodology described in Example 1 except that the plates were initially directly coated with a 100 µg/ml solution of the fusion protein described in Example 4 above. Table 9 summarizes the ELISA titers of these antiserums with the fusion protein.

TABLE 9

| Antiserum to: | Titers on fusion protein | SEQ ID NO |
|---|---|---|
| —Val—Asp—Pro—Arg—Leu—Glu—Pro—Trp—Lys—His—Pro—Gly—Ser— | >>8,000 | 28 |
| —Val—Asp—Pro—Asn—Leu—Glu—Pro—Trp—Lys—His—Pro—Gly—Ser— | >>8,000 | 47 |
| —Val—Asp—Pro—Lys—Leu— | >>8,000 | 45 |

TABLE 9-continued

| Antiserum to: | Titers on fusion protein | SEQ ID NO |
|---|---|---|
| Glu—Pro—Trp—Lys—His—Pro—Gly—Ser——Val—Asp—Pro—Ser—Leu—Glu—Pro—Trp—Lys—His—Pro—Gly—Ser— | >8,000 | 46 |
| —Arg—Gln—Arg—Arg—Arg—Ala—Pro—Gln—Asp—Ser— | 7,000 | 29 |
| —Arg—Gln—Arg—Arg—Arg—Ala—His—Gln—Asn—Ser— | >>8,000 | 52 |
| —Arg—Gln—Arg—Arg—Arg—Pro—Pro—Gln—Asp—Ser— | >8,000 | 53 |
| —Arg—Gln—Arg—Gln—Arg—Ala—Pro—Asp—Ser—Ser— | 8,000 | 82 |

These data show that the variant epitope sequences, expressed as a linear recombinant fusion protein, are expressed in a conformation recognizable by antibodies to the corresponding synthetic peptides.

B. Immunization of mice with the fusion protein

Three mice were immunized with 10 µg each of an aqueous solution of the fusion protein of Example 4 emulsified with an equal volume of Freund's complete adjuvant, given intraperitoneally. Two weeks later they were similarly boosted, except that Freund's incomplete adjuvant was used. Serums were obtained three weeks later.

C. ELISA testing of antiserums to the fusion protein with synthetic peptides corresponding to the epitope variants incorporated in the fusion protein ELISA testing was performed as described in Example 1 except that horseradish peroxidase conjugated anti-mouse immunoglobulin was used to detect antibody binding. The results are summarized in Table 10 below.

These data demonstrate that both epitope 1 and epitope 2 sequences are expressed in the linear fusion protein, and react with antibodies to the synthetic sequences (see above). Antibodies to epitope 1 were detectably induced by the recombinant fusion protein under the conditions of this experiment in mice. Thus recombinant linear expression is effective for induction of specific antibodies to epitope 1. The apparent failure of this experiment to induce antibodies to epitope 2 sequences is believed to be probably due to low immunogenicity in mice or some other experimental factor. It is anticipated that additional experiments with a more immunogenic fusion partner than GFP will demonstrate that the epitope 2 sequences also induce antibody responses, and thus are useful components of the compositions of this invention.

TABLE 10A

| Detector peptides | Titer with antiserum to fusion protein | SEQ ID NO |
|---|---|---|
| —Val—Asp—Pro—Arg—Leu—Glu—Pro—Trp—Lys—His—Pro—Gly—Ser— | 2218 | 28 |
| —Val—Asp—Pro—Asn—Leu—Glu—Pro—Trp—Lys—His—Pro—Gly—Ser— | 3158 | 47 |
| —Val—Asp—Pro—Lys—Leu—Glu—Pro—Trp—Lys—His—Pro—Gly—Ser— | 2440 | 45 |
| —Val—Asp—Pro—Ser—Leu—Glu—Pro—Trp—Lys—His—Pro—Gly—Ser— | 3031 | 46 |
| —Val—Asn—Pro—Ser—Leu— | 3718 | 48 |

TABLE 10A-continued

| Detector peptides | Titer with antiserum to fusion protein | SEQ ID NO |
|---|---|---|
| Glu—Pro—Trp—Lys—His—Pro—Gly—Ser—<br>—Val—Asp—His—Arg—Leu—Glu—Pro—Trp—Lys—His—Pro—Gly—Ser— | 3223 | 49 |
| —Arg—Gln—Arg—Arg—Arg—Ala—Pro—Gln—Asp—Ser— | Background | 29 |
| —Arg—Gln—Arg—Arg—Arg—Ala—His—Gln—Asn—Ser— | Background | 52 |
| —Arg—Gln—Arg—Arg—Arg—Pro—Pro—Gln—Asp—Ser— | Background | 53 |
| —Arg—Gln—Arg—Gln—Arg—Ala—Pro—Asp—Ser—Ser— | Background | 82 |
| —Arg—Gln—Arg—Arg—Arg—Ala—Pro—Glu—Asp—Ser— | Background | 83 |
| —Arg—Gln—Arg—Arg—Arg—Pro—Pro—Gln—Gly—Ser— | Background | 59 |

TABLE 10B

| Detector peptides | Titer with antiserum to fusion protein | SEQ ID NO |
|---|---|---|
| —Arg—Gln—Arg—Arg—Gly—Pro—Pro—Gln—Gly—Ser— | Background | 60 |
| —Arg—Gln—Arg—Arg—Arg—Pro—Pro—Gln—Asn—Ser— | Background | 61 |
| —Arg—Gln—Arg—Arg—Arg—Ser—Pro—Gln—Asp—Ser— | Background | 62 |
| —Arg—Gln—Arg—Arg—Arg—Ser—Pro—Gln—Asn—Ser— | Background | 63 |
| —Arg—Gln—Arg—Arg—Arg—Thr—Pro—Gln—Ser—Ser— | Background | 64 |
| —Arg—Gln—Arg—Arg—Arg—Ala—His—Gln—Asp—Ser— | Background | 65 |
| —Arg—Gln—Arg—Arg—Arg—Ala—Pro—Pro—Asp—Ser— | Background | 66 |

EXAMPLE 6
PRIMATE ANIMAL STUDY

A study was conducted in ten juvenile male rhesus macaques to determine if the presence of antibodies to Tat protein, induced by a synthetic peptide of this invention prior to infection with immunodeficiency virus would attenuate infection and reduce levels of virus in plasma. HIV-1 does not infect monkeys, but a corresponding simian immunodeficiency virus (SIV) does. P. A. Luciw et al., *Proc. Natl. Acad. Sci. USA*, 92:7490 (1995) constructed an infectious recombinant virus (chimera) of $SIV_{mac239}$ and HIV-$1_{SF33}$ that does infect monkeys, typically causing an acute viremia that peaks around 2 weeks and subsequently subsides by week 8. In this chimeric construct, termed $SHIV_{SF33}$, the SIV nucleotides encoding tat, rev and env (gp160) of $SIV_{mac239}$ have been replaced with the corresponding region of HIV-$1_{SF33}$.

A. Immunization of monkeys

The monkeys were randomized into two groups.

Each monkey of group 1 (control group) was immunized with 0.4 mg diphtheria toxoid (Commonwealth Serum Laboratories, Victoria, Australia) with 0.25 mg threonyl muramyl dipeptide (T-MDP) in 0.5 ml water, this being emulsified with 0.5 ml MF75 adjuvant (Chiron Corp, Emeryville Calif.).

Each monkey of group 2 (test group) was immunized with 0.1 mg of the synthetic peptide Cys-Val-Asp-Pro-Asn-Leu-Glu-Pro-Trp-His-Pro-Gly-Ser-amide [SEQ ID NO: 84] coupled to 0.4 mg diphtheria toxoid [A. C. Lee et al., *Mol. Immunol.*, 17:749 (1980)]. The conjugate was dissolved in 0.5 ml water containing 0.25 mg T-MDP and emulsified with 0.5 ml MF75 adjuvant.

Each monkey was immunized at day 0 and day 28 (week 4) with two 0.5 ml intramuscular injections at two distinct sites. The synthetic peptide immunogen contained the B cell epitope, -Asp-Pro-Asn-Leu-Glu-Pro- [SEQ ID NO: 9] of the Tat protein of SF33 HIV-1 that is incorporated in the $SHIV_{SF33}$ molecular clone that was used to challenge the monkeys (see above).

B. Testing for antibodies to Tat protein

At day 42 (week 6), 2 weeks after the booster injection, serums were drawn and tested by ELISA for binding to Ser-Gly-Ser-Gly-Val-Asp-Pro-Asn-Leu-Glu-Pro-Trp-Lys-His-Pro-Gly-Ser-OH [SEQ ID NO: 85], as described above in Example 1.

The control monkeys had background titers ranging from 25 to 44, while the test group had titers of 1788 to 9588, as shown in Table 11 below.

TABLE 11

| CONTROL GROUP | | TEST GROUP | |
|---|---|---|---|
| Monkey # | Titer | Monkey # | Titer |
| 18782 | 30 | 18759 | 1788 |
| 18785 | 25 | 18789 | 5780 |
| 18786 | 30 | 18790 | 2718 |
| 18859 | 54 | 18863 | 4139 |
| 18908 | 46 | 18945 | 9588 |
| GEOMETRIC MEAN TITER (GMT): | 35 | | 4068 |

C. Viral Challenge

At day 49 (week 7) after initial immunization, all monkeys were given 1 ml of a 1/1000 dilution of animal titered $SHIV_{SF33}$ stock intravenously (challenge day 0). This corresponded to 50 animal infectious doses$_{50\%}$ (50 AID$_{50}$) or 200 tissue culture infectious doses$_{50\%}$ (200 TCID$_{50}$).

D. Assessment of infection

Plasma was drawn in EDTA at weeks 2, 4 and 8, and copies of viral RNA per ml of plasma were measured by QR-RT-PCR, using SIV probes for the SIV component of $SHIV_{SF33}$ [A. J. Conrad et al., *J. Acq. Imm. Def. Syndrome and Hum. Retrovirol.*, 10:425 (1995)].

The results are summarized as follows in Table 12.

TABLE 12

| | SHIV RNA copies/ml plasma | | |
|---|---|---|---|
| Monkey # | 2 weeks | 4 weeks | 8 weeks |
| CONTROL GROUP | | | |
| 18782 | 880,000 | 30,000 | <500 |
| 18785 | 610,000 | 80,000 | <500 |
| 18786 | 500,000 | 50,000 | <500 |
| 18859 | 22,000,000 | 120,000 | <500 |
| 18908 | 20,000,000 | 100,000 | 1,000 |
| GEOMETRIC MEAN: TEST GROUP | 2,596,851 | 67,869 | |
| 18759 | 920,000 | 60,000 | <500 |
| 18789 | 950,000 | 50,000 | <500 |
| 18790 | 390,000 | 17,000 | <500 |
| 18863 | 2,000,000 | 27,000 | <500 |
| 18945 | 330,000 | 65,000 | 500 |

TABLE 12-continued

| | SHIV RNA copies/ml plasma | | |
|---|---|---|---|
| Monkey # | 2 weeks | 4 weeks | 8 weeks |
| GEOMETRIC MEAN: | 742,034 | 38,938 | |
| INHIBITION, TEST VERSUS CONTROLS: | 71% | 43% | |

As expected, $SHIV_{SF33}$ caused an acute infection, with peak levels of viral RNA at 2 weeks and barely or non-detectable levels by week 8. Monkeys immunized with a synthetic peptide conjugate that induced antibodies to the Tat protein of the challenge $SHIV_{SF33}$ virus had, by comparison with control immunized monkeys, a 71% reduction in peak virus levels in plasma 2 weeks after viral challenge, with a 43% inhibition being still detectable in the subsiding plasma viral levels at 4 weeks. This shows that SHIV multiplication in vivo was inhibited in the presence of antibodies to the Tat protein being utilized by the virus, and suggests that a similar effect would prevail in HIV infected humans.

E. Assessment of seroconversion

Subjects infected with HIV develop antibodies to virion surface proteins and this is detected by ELISA and used to diagnose infection. Monkey serums were tested prior to virus challenge and 8 weeks after challenge, using the HIVAB®HIV-1/HIV-2(rDNA)EIA (Abbott Labs, Illinois). All pre-challenge serums were negative and all 8 week post challenge serums were positive. These findings provide additional support for the fact that antibodies to Tat protein do not register in diagnostic assays for HIV seroconversion.

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

---

What is claimed is:

1. A composition comprising peptides or polypeptides comprising at least two or more amino acid sequences, selected from the group consisting of:
   -Asp-Pro-Arg-Leu-Glu-Pro- SEQ ID NO: 6;
   -Asp-Pro-Lys-Leu-Glu-Pro- SEQ ID NO: 7;
   -Asp-Pro-Ser-Leu-Glu-Pro- SEQ ID NO: 8; and
   -Asp-Pro-Asn-Leu-Glu-Pro- SEQ ID NO: 9,
said composition demonstrating a biological activity of inducing antibodies that react with HIV-1 Tat proteins from different HIV-1 strains or subtypes.

2. The composition according to claim 1 comprising one or more copies of each amino acid sequence of said group.

3. The composition according to claim 1, further comprising additional peptides and polypeptides, which comprise at least one amino acid sequence selected from the group consisting of:
   -Gly-Pro-Arg-Leu-Glu-Pro- SEQ ID NO: 11;
   -Ala-Pro-Arg-Leu-Glu-Pro- SEQ ED NO: 12;
   -His-Pro-Arg-Leu-Glu-Pro- SEQ ID NO: 13;
   -Asp-Pro-Gly-Leu-Glu-Pro- SEQ ID NO: 14;
   -Asp-Pro-Arg-Ile-Glu-Pro- SEQ ID NO: 15;
   -Asp-Pro-Arg-Leu-Gly-Pro- SEQ ID NO: 16;
   -Asp-Pro-Arg-Leu-Glu-Ala- SEQ ID NO: 17; and
   -Asn-Pro-Ser-Leu-Glu-Pro- SEQ ID NO: 18.

4. The composition according to claim 1, further comprising additional peptides and polypeptides, which comprise at least on e amino acid sequence of the formula -Arg-Arg-X-Pro-Gln-Y-Ser- SEQ ID NO: 10, wherein X is selected from the group consisting of Ala, Pro, Ser and Gln; and Y is selected from the group consisting of Asp, Asn, Gly and Ser.

5. The composition according to claim 4 wherein said additional peptide or polypeptide comprises one or multiple copies of the amino acid sequence -Arg-Arg-Ala-Pro-Gln-Asp-Ser- SEQ ID NO: 19.

6. The composition according to claim 4, further comprising additional peptides and polypeptides, which comprise at least one or more amino acid sequences selected from the group consisting of
   -Arg-Arg-Ala-Pro-Pro-Asp-Ser- SEQ ID NO: 20; and
   -Arg-Arg-Ala-Pro-Pro-Asp-Asn SEQ ID NO: 50.

7. The composition according to claim 4, further comprising additional peptides and polypeptides, which comprise at least one or more amino acid sequences selected from the group consisting of
   -Arg-Arg-Ala-His-Gln-Asp-Ser- SEQ ID NO: 21, and
   -Arg-Arg-Ala-His-Gln-Asn-Ser- SEQ ID NO: 22.

8. The composition according to claim 4, further comprising additional peptides and polypeptides, which comprise at least one or more amino acid sequences selected from the group consisting of
   -Arg-Arg-Pro-Pro-Gln-Asp-Asn- SEQ ID NO: 23;
   -Arg-Arg-Ala-Pro-Gln-Gly-Asn- SEQ ID NO: 51;
   -Arg-Gly-Ala-Pro-Gln-Asp-Ser- SEQ ID NO: 25;
   -Arg-Arg-Ala-Pro-Glu-Asp-Ser- SEQ ID NO: 26;

-Arg-Arg-Ala-Pro-Gln-Asp-Arg- SEQ ID NO: 24; and

-Arg-Arg-Ala-Ser-Gln-Asp-Ser- SEQ ID NO: 27.

9. The composition according to any of claims 1 to 8, wherein any one of said amino acid sequences is repeated multiple times in a single peptide or polypeptide.

10. The composition according to any of claims 1 to 8, wherein more than one of said amino acid sequences are repeated in a single peptide or polypeptide.

11. The composition according to any of claims 1 to 8, wherein each said peptide or polypeptide is coupled to the same or different carrier protein.

12. The composition according to claim 11, wherein said carrier protein is selected from the group consisting of an *E. coli* DnaK protein, a GST protein, a mycobacterial heat shock protein 70, a diphtheria toxoid, a tetanus toxoid, a galactokinase, an ubiquitin, an α-mating factor, a β-galactosidase, and an influenza NS-1 protein.

13. The composition according to any one of claims 1 to 8, wherein said peptides or polypeptides are present in the form of a multiple antigenic peptide.

14. The composition according to any one of claims 1 to 8, wherein said peptide or polypeptide is produced by chemical synthesis.

15. The composition according to any one of claims 1 to 8, wherein said peptide or polypeptide is produced recombinantly.

16. The composition according to claim 1, comprising peptides or polypeptides comprising at least three amino acid sequences selected from said group.

17. The composition according to claim 1, comprising peptides or polypeptides comprising all four amino acid sequences selected from said group.

18. A method for producing antibodies to HIV-1 Tat proteins from different HIV-1 strains or subtypes, said method comprising:
  (a) immunizing a mammal with a composition of any of claims 1 to 8; and
  (b) isolating and purifying said antibodies from said immunized mammal in sterile form.

19. A pharmaceutical composition comprising peptides or polypeptides comprising at least two or more amino acid sequences, selected from the group consisting of:
  -Asp-Pro-Arg-Leu-Glu-Pro- SEQ ID NO: 6;
  -Asp-Pro-Lys-Leu-Glu-Pro- SEQ ID NO: 7;
  -Asp-Pro-Ser-Leu-Glu-Pro- SEQ ID NO: 8; and
  -Asp-Pro-Asn-Leu-Glu-Pro- SEQ ID NO: 9, and a pharmaceutically acceptable carrier, said pharmaceutical composition useful for inducing antibodies that react with HIV-1 Tat proteins from different HIV-1 strains or subtypes.

20. The pharmaceutical composition according to claim 19 wherein said peptides or polypeptides are produced recombinantly or synthetically.

21. The pharmaceutical composition according to claim 19, further comprising an adjuvant.

22. The pharmaceutical composition according to claim 19, comprising peptides or polypeptides comprising at least three amino acid sequences selected from said group.

23. The pharmaceutical composition according to claim 19, comprising peptides or polypeptides comprising all four amino acid sequences selected from said group.

24. The pharmaceutical composition according to claim 19, further comprising peptides or polypeptides, which comprise at least one amino acid sequence selected from the group consisting of:

-Gly-Pro-Arg-Leu-Glu-Pro- SEQ ID NO: 11;
-Ala-Pro-Arg-Leu-Glu-Pro- SEQ ID NO: 12;
-His-Pro-Arg-Leu-Glu-Pro- SEQ ID NO: 13;
-Asp-Pro-Gly-Leu-Glu-Pro- SEQ ID NO: 14;
-Asp-Pro-Arg-Ile-Glu-Pro- SEQ ID NO: 15;
-Asp-Pro-Arg-Leu-Gly-Pro- SEQ ID NO: 16;
-Asp-Pro-Arg-Leu-Glu-Ala- SEQ ID NO: 17; and
-Asn-Pro-Ser-Leu-Glu-Pro- SEQ ID NO: 18.

25. The pharmaceutical composition according to claim 19, further comprising peptides or polypeptides, which comprise at least one amino acid sequence of the formula -Arg-Arg-X-Pro-Gln-Y-Ser- SEQ ID NO: 10, wherein X is selected from the group consisting of Ala, Pro, Ser and Gln; and Y is selected from the group consisting of Asp, Asn, Gly and Ser.

26. The pharmaceutical composition according to claim 25, wherein said amino acid sequence is -Arg-Arg-Ala-Pro-Gln-Asp-Ser- SEQ ID NO: 19.

27. The pharmaceutical composition according to claim 19, further comprising antibodies directed against peptides or polypeptides, which comprise at least one or more amino acid sequences selected from the group consisting of
  -Arg-Arg-Ala-Pro-Pro-Asp-Ser- SEQ ID NO: 20; and
  -Arg-Arg-Ala-Pro-Pro-Asp-Asn- SEQ ID NO: 50.

28. The pharmaceutical composition according to claim 19, further comprising peptides and polypeptides, which comprise at least one or more amino acid sequences selected from the group consisting of
  -Arg-Arg-Ala-His-Gln-Asp-Ser- SEQ ID NO: 21, and
  -Arg-Arg-Ala-His-Gln-Asn-Ser- SEQ ID NO: 22.

29. The composition according to claim 19, further comprising peptides and polypeptides, which comprise at least one or more amino acid sequences selected from the group consisting of
  -Arg-Arg-Pro-Pro-Gln-Asp-Asn- SEQ ID NO: 23;
  -Arg-Arg-Ala-Pro-Gln-Gly-Asn- SEQ ID NO: 51;
  -Arg-Gly-Ala-Pro-Gln-Asp-Ser- SEQ ID NO: 25;
  -Arg-Arg-Ala-Pro-Glu-Asp-Ser- SEQ ID NO: 26;
  -Arg-Arg-Ala-Pro-Gln-Asp-Arg- SEQ ID NO: 24; and
  -Arg-Arg-Ala-Ser-Gln-Asp-Ser- SEQ ID NO: 27.

30. The pharmaceutical composition according to any of claims 19 to 29, wherein any one of said amino acid sequences is repeated multiple times in a single peptide or polypeptide.

31. The pharmaceutical composition according to any of claims 19 to 29, wherein more than one of said amino acid sequences are repeated in a single peptide or polypeptide.

32. The pharmaceutical composition according to any of claims 19 to 29, wherein each said peptide or polypeptide is coupled to the same or different carrier protein.

33. The pharmaceutical composition according to any one of claims 19 to 29, wherein said peptides or polypeptides are present in the form of a multiple antigenic peptide.

34. A composition comprising:
  (a) a peptide or polypeptide comprising the amino acid sequence -Asp-Pro-Arg-Leu-Glu-Pro- SEQ ID NO: 6;
  (b) a peptide or polypeptide comprising the amino acid sequence -Asp-Pro-Lys-Leu-Glu-Pro- SEQ ID NO: 7;
  (c) a peptide or polypeptide comprising the amino acid sequence -Asp-Pro-Ser-Leu-Glu-Pro- SEQ ID NO: 8; and
  (d) a peptide or polypeptide comprising the amino acid sequence -Asp-Pro-Asn-Leu-Glu-Pro- SEQ ID NO: 9, said composition demonstrating a biological activity of inducing antibodies that react with HIV-1 Tat proteins from different HIV-1 strains or subtypes.

35. A pharmaceutical composition comprising:
(a) a peptide or polypeptide comprising the amino acid sequence -Asp-Pro-Arg-Leu-Glu-Pro- SEQ ID NO: 6;
(b) a peptide or polypeptide comprising the amino acid sequence -Asp-Pro-Lys-Leu-Glu-Pro- SEQ ID NO: 7;
(c) a peptide or polypeptide comprising the amino acid sequence -Asp-Pro-Ser-Leu-Glu-Pro- SEQ ID NO: 8, and
(d) a peptide or polypeptide comprising the amino acid sequence -Asp-Pro-Asn-Leu-Glu-Pro- SEQ ID NO: 9, and
(e) a pharmaceutically acceptable carrier, said pharmaceutical composition useful for inducing antibodies that react with HIV-1 Tat proteins from different HIV-1 strains or subtypes.

* * * * *

UNITED STATES PATENT AND TRADEMARK OFFICE
CERTIFICATE OF CORRECTION

PATENT NO. : 5,891,994
DATED : April 6, 1999
INVENTOR(S) : Gideon Goldstein

It is certified that error appears in the above-identified patent and that said Letters Patent is hereby corrected as shown below:

Col. 19, in Table I-continued, in the first sequence, delete the second occurrence of "Glu".

Col. 20, line 37, change "LYs" to -- Lys --.

Col. 67, line 66, replace "on e" with -- one --.

Signed and Sealed this

Thirtieth Day of November, 1999

Q. TODD DICKINSON

Attest:

Attesting Officer

Acting Commissioner of Patents and Trademarks

SEQUENCE LISTING ( 1 ) GENERAL INFORMATION:

( i i i ) NUMBER OF SEQUENCES: 85

( 2 ) INFORMATION FOR SEQ ID NO:1:

( i ) SEQUENCE CHARACTERISTICS:
        ( A ) LENGTH: 72 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:1:

```
Met Glu Pro Val Asp Pro Arg Leu Glu Pro Trp Lys His Pro Gly Ser
 1               5                  10                  15

Gln Pro Lys Thr Ala Cys Thr Asn Cys Tyr Cys Lys Lys Cys Cys Phe
            20                  25                  30

His Cys Gln Val Cys Phe Thr Thr Lys Gly Leu Gly Ile Ser Tyr Gly
        35                  40                  45

Arg Lys Lys Arg Arg Gln Arg Arg Ala Pro Gln Asp Ser Gln Thr
    50                  55                  60

His Gln Val Ser Leu Ser Lys Gln
65                  70
```

( 2 ) INFORMATION FOR SEQ ID NO:2:

( i ) SEQUENCE CHARACTERISTICS:
        ( A ) LENGTH: 912 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: join(1..876, 883..912)

( x i ) SEQUENCE DESCRIPTION: SEQ ID NO:2:

```
GAG CTC TAC AAA TCC GGG GAT CCG GGT GAA GAT CCG CGT TTA GAG CCG    48
Glu Leu Tyr Lys Ser Gly Asp Pro Gly Glu Asp Pro Arg Leu Glu Pro
```

| | | | | | | | | | | | | | | | | |
|---|---|---|---|---|---|---|---|---|---|---|---|---|---|---|---|---|
| | 1 | | | | 5 | | | | | 10 | | | | | 15 | |
| TGG | AAA | CAC | CCG | GGT | TCT | GGT | TCT | GTT | GAC | CCT | AAC | CTT | GAA | CCT | TGG | 96 |
| Trp | Lys | His | Pro | Gly | Ser | Gly | Ser | Val | Asp | Pro | Asn | Leu | Glu | Pro | Trp | |
| | | | 20 | | | | | 25 | | | | | 30 | | | |
| AAG | CAT | CCT | GGC | AGC | TCC | GGA | GTC | GAT | CCC | AAA | CTC | GAG | CCC | TGG | AAA | 144 |
| Lys | His | Pro | Gly | Ser | Ser | Gly | Val | Asp | Pro | Lys | Leu | Glu | Pro | Trp | Lys | |
| | | 35 | | | | | 40 | | | | | 45 | | | | |
| CAC | CCC | GGA | AGT | TCG | GGG | GTA | GAC | CCA | TCT | CTG | GAA | CCA | TGG | AAG | CAT | 192 |
| His | Pro | Gly | Ser | Ser | Gly | Val | Asp | Pro | Ser | Leu | Glu | Pro | Trp | Lys | His | |
| | | 50 | | | | | 55 | | | | | 60 | | | | |
| CCA | GGG | AGT | GGT | AGC | GTG | AAT | CCG | TCA | TTA | GAG | CCG | TGG | AAA | CAC | CCG | 240 |
| Pro | Gly | Ser | Gly | Ser | Val | Asn | Pro | Ser | Leu | Glu | Pro | Trp | Lys | His | Pro | |
| 65 | | | | | 70 | | | | | 75 | | | | | 80 | |
| GGT | TCA | TCT | GGA | GTT | GAT | CCT | CGC | TTG | GAA | CCT | TGG | GAG | CAT | CCT | GGT | 288 |
| Gly | Ser | Ser | Gly | Val | Asp | Pro | Arg | Leu | Glu | Pro | Trp | Glu | His | Pro | Gly | |
| | | | | 85 | | | | | 90 | | | | | 95 | | |
| TCG | TCC | GGT | GTA | GAC | CCC | CGA | CTT | GAG | CCC | TGG | AAT | CAC | CTC | GGG | AGT | 336 |
| Ser | Ser | Gly | Val | Asp | Pro | Arg | Leu | Glu | Pro | Trp | Asn | His | Leu | Gly | Ser | |
| | | | 100 | | | | | 105 | | | | | 110 | | | |
| TCA | GGC | GTA | GAT | CAT | CGG | CTC | GAA | CCA | TGG | AAA | CAT | CCA | GGT | TCT | GGA | 384 |
| Ser | Gly | Val | Asp | His | Arg | Leu | Glu | Pro | Trp | Lys | His | Pro | Gly | Ser | Gly | |
| | | 115 | | | | | 120 | | | | | 125 | | | | |
| GAT | CTG | CGC | CAG | CGG | CGA | CGT | ACT | CCT | CAG | GAT | TCT | GGA | TCT | CGA | CAA | 432 |
| Asp | Leu | Arg | Gln | Arg | Arg | Arg | Thr | Pro | Gln | Asp | Ser | Gly | Ser | Arg | Gln | |
| | 130 | | | | | 135 | | | | | 140 | | | | | |
| CGT | CGG | CGC | CCT | CCC | CAA | GAC | TCC | TCA | GGA | CGG | CAG | CGC | CGA | CGA | CCC | 480 |
| Arg | Arg | Arg | Pro | Pro | Gln | Asp | Ser | Ser | Gly | Arg | Gln | Arg | Arg | Arg | Pro | |
| 145 | | | | | 150 | | | | | 155 | | | | | 160 | |
| CCA | CAG | GGT | TCA | GGT | TCA | CGT | CAA | CGA | CGC | GGT | CCA | CCC | CAA | GGC | TCG | 528 |
| Pro | Gln | Gly | Ser | Gly | Ser | Arg | Gln | Arg | Arg | Gly | Pro | Pro | Gln | Gly | Ser | |
| | | | | 165 | | | | | 170 | | | | | 175 | | |
| GGT | TCG | CGC | CAG | CGG | CGA | CGT | CCG | CCT | CAG | AAC | TCT | AGT | GGA | CGA | CAA | 576 |
| Gly | Ser | Arg | Gln | Arg | Arg | Arg | Pro | Pro | Gln | Asn | Ser | Ser | Gly | Arg | Gln | |
| | | | 180 | | | | | 185 | | | | | 190 | | | |
| CGT | CGG | CGC | TCT | CCC | CAA | GAT | TCC | GGC | GGG | CGG | CAG | CGC | CGT | CGA | TCA | 624 |
| Arg | Arg | Arg | Ser | Pro | Gln | Asp | Ser | Gly | Gly | Arg | Gln | Arg | Arg | Arg | Ser | |
| | | 195 | | | | | 200 | | | | | 205 | | | | |
| CCA | CAG | AAC | TCA | GGT | GGG | CGT | CAA | CGA | CGC | CGG | ACT | CCG | CAA | TCT | TCA | 672 |
| Pro | Gln | Asn | Ser | Gly | Gly | Arg | Gln | Arg | Arg | Arg | Thr | Pro | Gln | Ser | Ser | |
| | 210 | | | | | 215 | | | | | 220 | | | | | |
| TCC | GGC | CGC | CAG | CGG | CGA | CGT | GCC | CAT | CAG | AAT | AGC | GGC | AGC | CGA | CAA | 720 |
| Ser | Gly | Arg | Gln | Arg | Arg | Arg | Ala | His | Gln | Asn | Ser | Gly | Ser | Arg | Gln | |
| 225 | | | | | 230 | | | | | 235 | | | | | 240 | |
| CGT | CGG | CGC | GCA | CAC | CAA | GAC | AGC | AGT | GGG | CGG | CAG | CGC | CGT | CGA | GCG | 768 |
| Arg | Arg | Arg | Ala | His | Gln | Asp | Ser | Ser | Gly | Arg | Gln | Arg | Arg | Arg | Ala | |
| | | | | 245 | | | | | 250 | | | | | 255 | | |
| CCT | GAA | GAT | AGT | GGT | TCT | CGT | CAA | CGA | CGC | CGG | GCT | CCC | CCT | GAC | AGC | 816 |
| Pro | Glu | Asp | Ser | Gly | Ser | Arg | Gln | Arg | Arg | Arg | Ala | Pro | Pro | Asp | Ser | |
| | | | 260 | | | | | 265 | | | | | 270 | | | |
| TCC | GGA | CGC | CAG | CGG | CAA | CGT | GCA | CCA | GAT | AGT | TCC | TCA | GGT | CAT | CAC | 864 |
| Ser | Gly | Arg | Gln | Arg | Gln | Arg | Ala | Pro | Asp | Ser | Ser | Ser | Gly | His | His | |
| | | 275 | | | | | 280 | | | | | 285 | | | | |
| CAC | CAT | CAT | CAC | TAATAA | GAA | TTC | GGA | TCC | TCT | AGA | GTC | GAC | AAG | CTT | | 912 |
| His | His | His | His | | Glu | Phe | Gly | Ser | Ser | Arg | Val | Asp | Lys | Leu | | |
| | 290 | | | | | 295 | | | | | 300 | | | | | |

( 2 ) INFORMATION FOR SEQ ID NO:3:

( i ) SEQUENCE CHARACTERISTICS:
        ( A ) LENGTH: 302 amino acids
        ( B ) TYPE: amino acid (D) TOPOLOGY: linear (ii) MOLECULE TYPE: protein (xi) SEQUENCE DESCRIPTION: SEQ ID NO:3:

| Glu | Leu | Tyr | Lys | Ser | Gly | Asp | Pro | Gly | Glu | Asp | Pro | Arg | Leu | Glu | Pro |
|---|---|---|---|---|---|---|---|---|---|---|---|---|---|---|---|
| 1 | | | | 5 | | | | | 10 | | | | | 15 | |

| Trp | Lys | His | Pro | Gly | Ser | Gly | Ser | Val | Asp | Pro | Asn | Leu | Glu | Pro | Trp |
|---|---|---|---|---|---|---|---|---|---|---|---|---|---|---|---|
| | | | 20 | | | | | 25 | | | | | 30 | | |

| Lys | His | Pro | Gly | Ser | Ser | Gly | Val | Asp | Pro | Lys | Leu | Glu | Pro | Trp | Lys |
|---|---|---|---|---|---|---|---|---|---|---|---|---|---|---|---|
| | | 35 | | | | | 40 | | | | | 45 | | | |

| His | Pro | Gly | Ser | Ser | Gly | Val | Asp | Pro | Ser | Leu | Glu | Pro | Trp | Lys | His |
|---|---|---|---|---|---|---|---|---|---|---|---|---|---|---|---|
| | 50 | | | | | 55 | | | | | 60 | | | | |

| Pro | Gly | Ser | Gly | Ser | Val | Asn | Pro | Ser | Leu | Glu | Pro | Trp | Lys | His | Pro |
|---|---|---|---|---|---|---|---|---|---|---|---|---|---|---|---|
| 65 | | | | | 70 | | | | | 75 | | | | | 80 |

| Gly | Ser | Ser | Gly | Val | Asp | Pro | Arg | Leu | Glu | Pro | Trp | Glu | His | Pro | Gly |
|---|---|---|---|---|---|---|---|---|---|---|---|---|---|---|---|
| | | | | 85 | | | | | 90 | | | | | 95 | |

| Ser | Ser | Gly | Val | Asp | Pro | Arg | Leu | Glu | Pro | Trp | Asn | His | Leu | Gly | Ser |
|---|---|---|---|---|---|---|---|---|---|---|---|---|---|---|---|
| | | | 100 | | | | | 105 | | | | | 110 | | |

| Ser | Gly | Val | Asp | His | Arg | Leu | Glu | Pro | Trp | Lys | His | Pro | Gly | Ser | Gly |
|---|---|---|---|---|---|---|---|---|---|---|---|---|---|---|---|
| | | | 115 | | | | | 120 | | | | | 125 | | |

| Asp | Leu | Arg | Gln | Arg | Arg | Arg | Thr | Pro | Gln | Asp | Ser | Gly | Ser | Arg | Gln |
|---|---|---|---|---|---|---|---|---|---|---|---|---|---|---|---|
| | 130 | | | | | 135 | | | | | 140 | | | | |

| Arg | Arg | Arg | Pro | Pro | Gln | Asp | Ser | Ser | Gly | Arg | Gln | Arg | Arg | Arg | Pro |
|---|---|---|---|---|---|---|---|---|---|---|---|---|---|---|---|
| 145 | | | | | 150 | | | | | 155 | | | | | 160 |

| Pro | Gln | Gly | Ser | Gly | Ser | Arg | Gln | Arg | Arg | Gly | Pro | Pro | Gln | Gly | Ser |
|---|---|---|---|---|---|---|---|---|---|---|---|---|---|---|---|
| | | | | 165 | | | | | 170 | | | | | 175 | |

| Gly | Ser | Arg | Gln | Arg | Arg | Arg | Pro | Pro | Gln | Asn | Ser | Ser | Gly | Arg | Gln |
|---|---|---|---|---|---|---|---|---|---|---|---|---|---|---|---|
| | | | 180 | | | | | 185 | | | | | 190 | | |

| Arg | Arg | Arg | Ser | Pro | Gln | Asp | Ser | Gly | Gly | Arg | Gln | Arg | Arg | Arg | Ser |
|---|---|---|---|---|---|---|---|---|---|---|---|---|---|---|---|
| | | 195 | | | | | 200 | | | | | 205 | | | |

| Pro | Gln | Asn | Ser | Gly | Gly | Arg | Gln | Arg | Arg | Arg | Thr | Pro | Gln | Ser | Ser |
|---|---|---|---|---|---|---|---|---|---|---|---|---|---|---|---|
| | 210 | | | | | 215 | | | | | 220 | | | | |

| Ser | Gly | Arg | Gln | Arg | Arg | Arg | Ala | His | Gln | Asn | Ser | Gly | Ser | Arg | Gln |
|---|---|---|---|---|---|---|---|---|---|---|---|---|---|---|---|
| 225 | | | | | 230 | | | | | 235 | | | | | 240 |

| Arg | Arg | Arg | Ala | His | Gln | Asp | Ser | Ser | Gly | Arg | Gln | Arg | Arg | Arg | Ala |
|---|---|---|---|---|---|---|---|---|---|---|---|---|---|---|---|
| | | | | 245 | | | | | 250 | | | | | 255 | |

| Pro | Glu | Asp | Ser | Gly | Ser | Arg | Gln | Arg | Arg | Arg | Ala | Pro | Pro | Asp | Ser |
|---|---|---|---|---|---|---|---|---|---|---|---|---|---|---|---|
| | | | 260 | | | | | 265 | | | | | 270 | | |

| Ser | Gly | Arg | Gln | Arg | Gln | Arg | Ala | Pro | Asp | Ser | Ser | Ser | Gly | His | His |
|---|---|---|---|---|---|---|---|---|---|---|---|---|---|---|---|
| | | 275 | | | | | 280 | | | | | 285 | | | |

| His | His | His | His | Glu | Phe | Gly | Ser | Ser | Arg | Val | Asp | Lys | Leu |
|---|---|---|---|---|---|---|---|---|---|---|---|---|---|
| | 290 | | | | | 295 | | | | | 300 | | |

(2) INFORMATION FOR SEQ ID NO:4:

(i) SEQUENCE CHARACTERISTICS:
(A) LENGTH: 9 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:4:

| Arg | Lys | Lys | Arg | Arg | Gln | Arg | Arg | Arg |
|---|---|---|---|---|---|---|---|---|
| 1 | | | | 5 | | | | |

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:5:

Gly Arg Gly Asp Ser Pro
1                      5

( 2 ) INFORMATION FOR SEQ ID NO:6:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:6:

Asp Pro Arg Leu Glu Pro
1                      5

( 2 ) INFORMATION FOR SEQ ID NO:7:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:7:

Asp Pro Lys Leu Glu Pro
1                      5

( 2 ) INFORMATION FOR SEQ ID NO:8:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:8:

Asp Pro Ser Leu Glu Pro
1                      5

( 2 ) INFORMATION FOR SEQ ID NO:9:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:9:

Asp Pro Asn Leu Glu Pro
1                      5

( 2 ) INFORMATION FOR SEQ ID NO:10:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Active-site
        ( B ) LOCATION: 3
        ( D ) OTHER INFORMATION: /note= "the amino acid in position 3 may be Ala, Pro, Ser or Gln"

( i x ) FEATURE:
        ( A ) NAME/KEY: Active-site
        ( B ) LOCATION: 6
        ( D ) OTHER INFORMATION: /note= "the amino acid in position 6 may be Asp, Asn, Gly or Ser"

( x i ) SEQUENCE DESCRIPTION: SEQ ID NO:10:

Arg Arg Xaa Pro Gln Xaa Ser
    1                  5

( 2 ) INFORMATION FOR SEQ ID NO:11:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:11:

Gly Pro Arg Leu Glu Pro
    1                  5

( 2 ) INFORMATION FOR SEQ ID NO:12:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:12:

Ala Pro Arg Leu Glu Pro
    1                  5

( 2 ) INFORMATION FOR SEQ ID NO:13:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:13:

His Pro Arg Leu Glu Pro
    1                  5

( 2 ) INFORMATION FOR SEQ ID NO:14:

( i ) SEQUENCE CHARACTERISTICS:
        ( A ) LENGTH: 6 amino acids (B) TYPE: amino acid
(C) STRANDEDNESS:
(D) TOPOLOGY: linear (ii) MOLECULE TYPE: peptide (xi) SEQUENCE DESCRIPTION: SEQ ID NO:14:

Asp Pro Gly Leu Glu Pro
1               5

(2) INFORMATION FOR SEQ ID NO:15:

(i) SEQUENCE CHARACTERISTICS:
    (A) LENGTH: 6 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:15:

Asp Pro Arg Ile Glu Pro
1               5

(2) INFORMATION FOR SEQ ID NO:16:

(i) SEQUENCE CHARACTERISTICS:
    (A) LENGTH: 6 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:16:

Asp Pro Arg Leu Gly Pro
1               5

(2) INFORMATION FOR SEQ ID NO:17:

(i) SEQUENCE CHARACTERISTICS:
    (A) LENGTH: 6 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:17:

Asp Pro Arg Leu Glu Ala
1               5

(2) INFORMATION FOR SEQ ID NO:18:

(i) SEQUENCE CHARACTERISTICS:
    (A) LENGTH: 6 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:18:

Asn Pro Ser Leu Glu Pro
1               5

(2) INFORMATION FOR SEQ ID NO:19:

(i) SEQUENCE CHARACTERISTICS:
    (A) LENGTH: 7 amino acids (B) TYPE: amino acid
(C) STRANDEDNESS:
(D) TOPOLOGY: linear (ii) MOLECULE TYPE: peptide (xi) SEQUENCE DESCRIPTION: SEQ ID NO:19:

Arg Arg Ala Pro Gln Asp Ser
1               5

(2) INFORMATION FOR SEQ ID NO:20:

(i) SEQUENCE CHARACTERISTICS:
(A) LENGTH: 7 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:20:

Arg Arg Ala Pro Pro Asp Ser
1               5

(2) INFORMATION FOR SEQ ID NO:21:

(i) SEQUENCE CHARACTERISTICS:
(A) LENGTH: 7 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:21:

Arg Arg Ala His Gln Asp Ser
1               5

(2) INFORMATION FOR SEQ ID NO:22:

(i) SEQUENCE CHARACTERISTICS:
(A) LENGTH: 7 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:22:

Arg Arg Ala His Gln Asn Ser
1               5

(2) INFORMATION FOR SEQ ID NO:23:

(i) SEQUENCE CHARACTERISTICS:
(A) LENGTH: 7 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:23:

Arg Arg Pro Pro Gln Asp Asn
1               5

(2) INFORMATION FOR SEQ ID NO:24:

(i) SEQUENCE CHARACTERISTICS:
(A) LENGTH: 7 amino acids (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:24:

Arg Arg Ala Pro Gln Asp Arg
1               5

(2) INFORMATION FOR SEQ ID NO:25:

(i) SEQUENCE CHARACTERISTICS:
    (A) LENGTH: 7 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:25:

Arg Gly Ala Pro Gln Asp Ser
1               5

(2) INFORMATION FOR SEQ ID NO:26:

(i) SEQUENCE CHARACTERISTICS:
    (A) LENGTH: 7 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:26:

Arg Arg Ala Pro Glu Asp Ser
1               5

(2) INFORMATION FOR SEQ ID NO:27:

(i) SEQUENCE CHARACTERISTICS:
    (A) LENGTH: 7 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:27:

Arg Arg Ala Ser Gln Asp Ser
1               5

(2) INFORMATION FOR SEQ ID NO:28:

(i) SEQUENCE CHARACTERISTICS:
    (A) LENGTH: 13 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:28:

Val Asp Pro Arg Leu Glu Pro Trp Lys His Pro Gly Ser
1               5                   10

(2) INFORMATION FOR SEQ ID NO:29:

(i) SEQUENCE CHARACTERISTICS:
    (A) LENGTH: 10 amino acids (B) TYPE: amino acid
(C) STRANDEDNESS:
(D) TOPOLOGY: linear (ii) MOLECULE TYPE: peptide (xi) SEQUENCE DESCRIPTION: SEQ ID NO:29:

```
Arg Gln Arg Arg Arg Ala Pro Gln Asp Ser
1               5                   10
```

(2) INFORMATION FOR SEQ ID NO:30:

(i) SEQUENCE CHARACTERISTICS:
(A) LENGTH: 4 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:30:

```
Ser Gly Ser Gly
1
```

(2) INFORMATION FOR SEQ ID NO:31:

(i) SEQUENCE CHARACTERISTICS:
(A) LENGTH: 12 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:31:

```
Val Asp Pro Arg Leu Pro Trp Lys His Pro Gly Ser
1               5                   10
```

(2) INFORMATION FOR SEQ ID NO:32:

(i) SEQUENCE CHARACTERISTICS:
(A) LENGTH: 11 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:32:

```
Asp Pro Arg Leu Pro Trp Lys His Pro Gly Ser
1               5                   10
```

(2) INFORMATION FOR SEQ ID NO:33:

(i) SEQUENCE CHARACTERISTICS:
(A) LENGTH: 7 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:33:

```
Val Asp Pro Arg Leu Pro Trp
1               5
```

(2) INFORMATION FOR SEQ ID NO:34:

(i) SEQUENCE CHARACTERISTICS:
(A) LENGTH: 6 amino acids (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:34:

Val Asp Pro Arg Leu Pro
    1               5

(2) INFORMATION FOR SEQ ID NO:35:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:35:

Val Asp Pro Arg Leu
    1               5

(2) INFORMATION FOR SEQ ID NO:36:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:36:

Gln Arg Arg Arg Ala Pro Gln Asp Ser
    1               5

(2) INFORMATION FOR SEQ ID NO:37:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:37:

Arg Arg Arg Ala Pro Gln Asp Ser
    1               5

(2) INFORMATION FOR SEQ ID NO:38:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:38:

Arg Ala Pro Gln Asp Ser
    1               5

(2) INFORMATION FOR SEQ ID NO:39:

(i) SEQUENCE CHARACTERISTICS:
        (A) LENGTH: 9 amino acids (B) TYPE: amino acid
(C) STRANDEDNESS:
(D) TOPOLOGY: linear (ii) MOLECULE TYPE: peptide (xi) SEQUENCE DESCRIPTION: SEQ ID NO:39:

Arg Gln Arg Arg Arg Ala Pro Gln Asp
1               5

(2) INFORMATION FOR SEQ ID NO:40:

(i) SEQUENCE CHARACTERISTICS:
  (A) LENGTH: 8 amino acids
  (B) TYPE: amino acid
  (C) STRANDEDNESS:
  (D) TOPOLOGY: linear (ii) MOLECULE TYPE: peptide (xi) SEQUENCE DESCRIPTION: SEQ ID NO:40:

Arg Gln Arg Arg Arg Ala Pro Gln
1               5

(2) INFORMATION FOR SEQ ID NO:41:

(i) SEQUENCE CHARACTERISTICS:
  (A) LENGTH: 6 amino acids
  (B) TYPE: amino acid
  (C) STRANDEDNESS:
  (D) TOPOLOGY: linear (ii) MOLECULE TYPE: peptide (xi) SEQUENCE DESCRIPTION: SEQ ID NO:41:

Asp His Arg Leu Glu Pro
1               5

(2) INFORMATION FOR SEQ ID NO:42:

(i) SEQUENCE CHARACTERISTICS:
  (A) LENGTH: 6 amino acids
  (B) TYPE: amino acid
  (C) STRANDEDNESS:
  (D) TOPOLOGY: linear (ii) MOLECULE TYPE: peptide (xi) SEQUENCE DESCRIPTION: SEQ ID NO:42:

Asp Pro Asn Leu Asp Pro
1               5

(2) INFORMATION FOR SEQ ID NO:43:

(i) SEQUENCE CHARACTERISTICS:
  (A) LENGTH: 6 amino acids
  (B) TYPE: amino acid
  (C) STRANDEDNESS:
  (D) TOPOLOGY: linear (ii) MOLECULE TYPE: peptide (xi) SEQUENCE DESCRIPTION: SEQ ID NO:43:

Asp Pro Asn Ile Glu Pro
1               5

(2) INFORMATION FOR SEQ ID NO:44:

(i) SEQUENCE CHARACTERISTICS:
  (A) LENGTH: 6 amino acids (B) TYPE: amino acid
(C) STRANDEDNESS:
(D) TOPOLOGY: linear (ii) MOLECULE TYPE: peptide (xi) SEQUENCE DESCRIPTION: SEQ ID NO:44:

Asp Pro Asn Leu Glu Ser
1               5

(2) INFORMATION FOR SEQ ID NO:45:

(i) SEQUENCE CHARACTERISTICS:
    (A) LENGTH: 13 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:45:

Val Asp Pro Lys Leu Glu Pro Trp Lys His Pro Gly Ser
1               5                   10

(2) INFORMATION FOR SEQ ID NO:46:

(i) SEQUENCE CHARACTERISTICS:
    (A) LENGTH: 13 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:46:

Val Asp Pro Ser Leu Glu Pro Trp Lys His Pro Gly Ser
1               5                   10

(2) INFORMATION FOR SEQ ID NO:47:

(i) SEQUENCE CHARACTERISTICS:
    (A) LENGTH: 13 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:47:

Val Asp Pro Asn Leu Glu Pro Trp Lys His Pro Gly Ser
1               5                   10

(2) INFORMATION FOR SEQ ID NO:48:

(i) SEQUENCE CHARACTERISTICS:
    (A) LENGTH: 13 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:48:

Val Asn Pro Ser Leu Glu Pro Trp Lys His Pro Gly Ser
1               5                   10

(2) INFORMATION FOR SEQ ID NO:49:

(i) SEQUENCE CHARACTERISTICS:
    (A) LENGTH: 13 amino acids (B) TYPE: amino acid
(C) STRANDEDNESS:
(D) TOPOLOGY: linear (ii) MOLECULE TYPE: peptide (xi) SEQUENCE DESCRIPTION: SEQ ID NO:49:

```
Val Asp His Arg Leu Glu Pro Trp Lys His Pro Gly Ser
1               5                   10
```

(2) INFORMATION FOR SEQ ID NO:50:

(i) SEQUENCE CHARACTERISTICS:
(A) LENGTH: 7 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:50:

```
Arg Arg Ala Pro Pro Asp Asn
1               5
```

(2) INFORMATION FOR SEQ ID NO:51:

(i) SEQUENCE CHARACTERISTICS:
(A) LENGTH: 7 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:51:

```
Arg Arg Ala Pro Gln Gly Asn
1               5
```

(2) INFORMATION FOR SEQ ID NO:52:

(i) SEQUENCE CHARACTERISTICS:
(A) LENGTH: 10 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:52:

```
Arg Gln Arg Arg Arg Ala His Gln Asn Ser
1               5                   10
```

(2) INFORMATION FOR SEQ ID NO:53:

(i) SEQUENCE CHARACTERISTICS:
(A) LENGTH: 10 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:53:

```
Arg Gln Arg Arg Arg Pro Pro Gln Asp Ser
1               5                   10
```

(2) INFORMATION FOR SEQ ID NO:54:

(i) SEQUENCE CHARACTERISTICS:
(A) LENGTH: 11 amino acids (B) TYPE: amino acid
(C) STRANDEDNESS:
(D) TOPOLOGY: linear (i i) MOLECULE TYPE: peptide (x i) SEQUENCE DESCRIPTION: SEQ ID NO:54:

Gly Arg Gln Arg Arg Arg Ala Pro Gln Asp Ser
1               5                   10

(2) INFORMATION FOR SEQ ID NO:55:

(i) SEQUENCE CHARACTERISTICS:
    (A) LENGTH: 9 amino acids
    (B) TYPE: amino acid
    (C) STRANDEDNESS:
    (D) TOPOLOGY: linear (i i) MOLECULE TYPE: peptide (x i) SEQUENCE DESCRIPTION: SEQ ID NO:55:

Gly Arg Arg Ala His Gln Asp Ser Gly
1               5

(2) INFORMATION FOR SEQ ID NO:56:

(i) SEQUENCE CHARACTERISTICS:
    (A) LENGTH: 9 amino acids
    (B) TYPE: amino acid
    (C) STRANDEDNESS:
    (D) TOPOLOGY: linear (i i) MOLECULE TYPE: peptide (x i) SEQUENCE DESCRIPTION: SEQ ID NO:56:

Gly Arg Arg Ala Pro Pro Asn Ser Gly
1               5

(2) INFORMATION FOR SEQ ID NO:57:

(i) SEQUENCE CHARACTERISTICS:
    (A) LENGTH: 9 amino acids
    (B) TYPE: amino acid
    (C) STRANDEDNESS:
    (D) TOPOLOGY: linear (i i) MOLECULE TYPE: peptide (x i) SEQUENCE DESCRIPTION: SEQ ID NO:57:

Gly Arg Arg Ala Pro Pro Asn Ser Gly
1               5

(2) INFORMATION FOR SEQ ID NO:58:

(i) SEQUENCE CHARACTERISTICS:
    (A) LENGTH: 11 amino acids
    (B) TYPE: amino acid
    (C) STRANDEDNESS:
    (D) TOPOLOGY: linear (i i) MOLECULE TYPE: peptide (x i) SEQUENCE DESCRIPTION: SEQ ID NO:58:

Arg Arg Ala Pro Gln Asp Ser Gln Thr His Gln
1               5                   10

(2) INFORMATION FOR SEQ ID NO:59:

(i) SEQUENCE CHARACTERISTICS:
    (A) LENGTH: 10 amino acids (B) TYPE: amino acid
(C) STRANDEDNESS:
(D) TOPOLOGY: linear (ii) MOLECULE TYPE: peptide (xi) SEQUENCE DESCRIPTION: SEQ ID NO:59:

Arg Gln Arg Arg Arg Pro Pro Gln Gly Ser
1               5                   10

(2) INFORMATION FOR SEQ ID NO:60:

(i) SEQUENCE CHARACTERISTICS:
(A) LENGTH: 10 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:60:

Arg Gln Arg Arg Gly Pro Pro Gln Gly Ser
1               5                   10

(2) INFORMATION FOR SEQ ID NO:61:

(i) SEQUENCE CHARACTERISTICS:
(A) LENGTH: 10 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:61:

Arg Gln Arg Arg Arg Pro Pro Gln Asn Ser
1               5                   10

(2) INFORMATION FOR SEQ ID NO:62:

(i) SEQUENCE CHARACTERISTICS:
(A) LENGTH: 10 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:62:

Arg Gln Arg Arg Arg Ser Pro Gln Asp Ser
1               5                   10

(2) INFORMATION FOR SEQ ID NO:63:

(i) SEQUENCE CHARACTERISTICS:
(A) LENGTH: 10 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:63:

Arg Gln Arg Arg Arg Ser Pro Gln Asn Ser
1               5                   10

(2) INFORMATION FOR SEQ ID NO:64:

(i) SEQUENCE CHARACTERISTICS:
(A) LENGTH: 10 amino acids (B) TYPE: amino acid
(C) STRANDEDNESS:
(D) TOPOLOGY: linear (i i) MOLECULE TYPE: peptide (x i) SEQUENCE DESCRIPTION: SEQ ID NO:64:

```
Arg Gln Arg Arg Arg Thr Pro Gln Ser Ser
1               5                   10
```

(2) INFORMATION FOR SEQ ID NO:65:

(i) SEQUENCE CHARACTERISTICS:
(A) LENGTH: 10 amino acids
(B) TYPE: amino acid
(C) STRANDEDNESS:
(D) TOPOLOGY: linear (i i) MOLECULE TYPE: peptide (x i) SEQUENCE DESCRIPTION: SEQ ID NO:65:

```
Arg Gln Arg Arg Arg Ala His Gln Asp Ser
1               5                   10
```

(2) INFORMATION FOR SEQ ID NO:66:

(i) SEQUENCE CHARACTERISTICS:
(A) LENGTH: 10 amino acids
(B) TYPE: amino acid
(C) STRANDEDNESS:
(D) TOPOLOGY: linear (i i) MOLECULE TYPE: peptide (x i) SEQUENCE DESCRIPTION: SEQ ID NO:66:

```
Arg Gln Arg Arg Arg Ala Pro Pro Asp Ser
1               5                   10
```

(2) INFORMATION FOR SEQ ID NO:67:

(i) SEQUENCE CHARACTERISTICS:
(A) LENGTH: 7 amino acids
(B) TYPE: amino acid
(C) STRANDEDNESS:
(D) TOPOLOGY: linear (i i) MOLECULE TYPE: peptide (x i) SEQUENCE DESCRIPTION: SEQ ID NO:67:

```
Arg Arg Ala Pro Gln Asp Asn
1               5
```

(2) INFORMATION FOR SEQ ID NO:68:

(i) SEQUENCE CHARACTERISTICS:
(A) LENGTH: 7 amino acids
(B) TYPE: amino acid
(C) STRANDEDNESS:
(D) TOPOLOGY: linear (i i) MOLECULE TYPE: peptide (x i) SEQUENCE DESCRIPTION: SEQ ID NO:68:

```
Arg Arg Thr Pro Gln Gly Ser
1               5
```

(2) INFORMATION FOR SEQ ID NO:69:

(i) SEQUENCE CHARACTERISTICS:
(A) LENGTH: 7 amino acids (B) TYPE: amino acid
(C) STRANDEDNESS:
(D) TOPOLOGY: linear (ii) MOLECULE TYPE: peptide (xi) SEQUENCE DESCRIPTION: SEQ ID NO:69:

Arg Arg Ala Pro Gln Gly Ser
1               5

(2) INFORMATION FOR SEQ ID NO:70:

(i) SEQUENCE CHARACTERISTICS:
(A) LENGTH: 7 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:70:

Arg Arg Thr Pro Gln Asp Ser
1               5

(2) INFORMATION FOR SEQ ID NO:71:

(i) SEQUENCE CHARACTERISTICS:
(A) LENGTH: 7 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:71:

Arg Arg Pro Pro Gln Ser Ser
1               5

(2) INFORMATION FOR SEQ ID NO:72:

(i) SEQUENCE CHARACTERISTICS:
(A) LENGTH: 7 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:72:

Arg Arg Ala Pro Gln Asn Ser
1               5

(2) INFORMATION FOR SEQ ID NO:73:

(i) SEQUENCE CHARACTERISTICS:
(A) LENGTH: 7 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:73:

Arg Arg Ser Pro Gln Asp Ser
1               5

(2) INFORMATION FOR SEQ ID NO:74:

(i) SEQUENCE CHARACTERISTICS:
(A) LENGTH: 11 amino acids (B) TYPE: amino acid
(C) STRANDEDNESS:
(D) TOPOLOGY: linear (ii) MOLECULE TYPE: peptide (xi) SEQUENCE DESCRIPTION: SEQ ID NO:74:

Cys Arg Gln Arg Arg Arg Ala Pro Gln Asp Ser
1               5                   10

(2) INFORMATION FOR SEQ ID NO:75:

(i) SEQUENCE CHARACTERISTICS:
(A) LENGTH: 7 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:75:

Arg Arg Pro Pro Gln Asp Ser
1               5

(2) INFORMATION FOR SEQ ID NO:76:

(i) SEQUENCE CHARACTERISTICS:
(A) LENGTH: 7 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:76:

Arg Arg Pro Pro Gln Asn Ser
1               5

(2) INFORMATION FOR SEQ ID NO:77:

(i) SEQUENCE CHARACTERISTICS:
(A) LENGTH: 7 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:77:

Arg Arg Pro Pro Gln Gly Ser
1               5

(2) INFORMATION FOR SEQ ID NO:78:

(i) SEQUENCE CHARACTERISTICS:
(A) LENGTH: 7 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:78:

Arg Arg Ser Pro Gln Asn Ser
1               5

(2) INFORMATION FOR SEQ ID NO:79:

(i) SEQUENCE CHARACTERISTICS:
(A) LENGTH: 7 amino acids (B) TYPE: amino acid
(C) STRANDEDNESS:
(D) TOPOLOGY: linear (ii) MOLECULE TYPE: peptide (xi) SEQUENCE DESCRIPTION: SEQ ID NO:79:

Arg Arg Ala Pro Gln Ser Ser
1               5

(2) INFORMATION FOR SEQ ID NO:80:

(i) SEQUENCE CHARACTERISTICS:
(A) LENGTH: 7 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:80:

Arg Arg Ser Pro Gln Gly Ser
1               5

(2) INFORMATION FOR SEQ ID NO:81:

(i) SEQUENCE CHARACTERISTICS:
(A) LENGTH: 7 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:81:

Arg Arg Thr Pro Gln Asn Ser
1               5

(2) INFORMATION FOR SEQ ID NO:82:

(i) SEQUENCE CHARACTERISTICS:
(A) LENGTH: 10 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:82:

Arg Gln Arg Gln Arg Ala Pro Asp Ser Ser
1               5                   10

(2) INFORMATION FOR SEQ ID NO:83:

(i) SEQUENCE CHARACTERISTICS:
(A) LENGTH: 10 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:83:

Arg Gln Arg Arg Arg Ala Pro Glu Asp Ser
1               5                   10

(2) INFORMATION FOR SEQ ID NO:84:

(i) SEQUENCE CHARACTERISTICS:
(A) LENGTH: 13 amino acids

-continued (B) TYPE: amino acid
        (C) STRANDEDNESS:
        (D) TOPOLOGY: linear (ii) MOLECULE TYPE: peptide (ix) FEATURE:
        (A) NAME/KEY: Binding-site
        (B) LOCATION: 13
        (D) OTHER INFORMATION: /note= "an amide is attached to the Ser in position 13"

(xi) SEQUENCE DESCRIPTION: SEQ ID NO:84:

Cys Val Asp Pro Asn Leu Glu Pro Trp His Pro Gly Ser
1               5                   10

(2) INFORMATION FOR SEQ ID NO:85:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Binding-site
        (B) LOCATION: 17
        (D) OTHER INFORMATION: /note= "OH is attached to the Ser in position 17"

(xi) SEQUENCE DESCRIPTION: SEQ ID NO:85:

Ser Gly Ser Gly Val Asp Pro Asn Leu Glu Pro Trp Lys His Pro Gly
1               5                   10                  15
Ser